United States Patent
Mosoiu et al.

(10) Patent No.: US 7,879,618 B2
(45) Date of Patent: Feb. 1, 2011

(54) METHOD AND REAGENT FOR PRODUCING NARROW, HOMOGENOUS REAGENT STRIPS

(75) Inventors: Dan Mosoiu, Limburgerhof (DE); Christopher D. Wilsey, Carmel, IN (US)

(73) Assignees: Roche Diagnostics Operations, Inc., Indianapolis, IN (US); Roche Operations Ltd., Hamilton (BM)

( * ) Notice: Subject to any disclaimer, the term of this patent is extended or adjusted under 35 U.S.C. 154(b) by 199 days.

(21) Appl. No.: 12/361,830

(22) Filed: Jan. 29, 2009

(65) Prior Publication Data
US 2009/0162532 A1 Jun. 25, 2009

Related U.S. Application Data

(62) Division of application No. 10/871,966, filed on Jun. 18, 2004, now Pat. No. 7,749,437.

(60) Provisional application No. 60/480,397, filed on Jun. 20, 2003.

(51) Int. Cl.
*G01N 33/48* (2006.01)
(52) U.S. Cl. .................. 436/170; 436/166; 436/169; 422/58; 422/81
(58) Field of Classification Search ............... 436/166, 436/169, 170; 422/58, 61
See application file for complete search history.

(56) References Cited

U.S. PATENT DOCUMENTS

| | | |
|---|---|---|
| 3,715,192 A | 2/1973 | Wenz et al. |
| 3,980,437 A | 9/1976 | Kishimoto et al. |
| 4,065,263 A | 12/1977 | Woodbridge, III |
| 4,225,410 A | 9/1980 | Pace |
| 4,420,564 A | 12/1983 | Tsuji et al. |
| 4,476,149 A | 10/1984 | Poppe et al. |
| 4,510,383 A | 4/1985 | Ruppender |
| 4,545,382 A | 10/1985 | Higgins et al. |
| 4,571,292 A | 2/1986 | Liu et al. |
| 4,578,716 A | 3/1986 | Van Rijckevorsel et al. |
| 4,592,893 A | 6/1986 | Poppe et al. |
| 4,671,288 A | 6/1987 | Gough |
| 4,679,562 A | 7/1987 | Luksha |
| 4,714,874 A | 12/1987 | Morris et al. |

(Continued)

FOREIGN PATENT DOCUMENTS

CN    1 467 496 A    5/2003

(Continued)

OTHER PUBLICATIONS

Canadian Patent Application No. 2,529,579 Office Action mailed Nov. 26, 2009.

(Continued)

*Primary Examiner*—Lyle A Alexander
(74) *Attorney, Agent, or Firm*—Woodard Emhardt Moriarty McNett & Henry

(57) ABSTRACT

The present invention concerns a reagent coating mass which can be used in slot-die-coating of flat support materials in the manufacturing processes of test strips. Advantageously, the reagent mass of the invention exhibits certain superior rheological properties such as viscosity, surface tension and thixotropy. The reagent mass is preferably used to coat thin, narrow and homogeneous stripes of reagent material onto flat web material.

14 Claims, 9 Drawing Sheets

U.S. PATENT DOCUMENTS

| | | |
|---|---|---|
| 4,789,804 A | 12/1988 | Karube et al. |
| 4,797,256 A | 1/1989 | Watlington, IV |
| 4,805,624 A | 2/1989 | Yao et al. |
| 4,877,580 A | 10/1989 | Aronowitz et al. |
| 4,897,173 A | 1/1990 | Nankai et al. |
| 4,927,516 A | 5/1990 | Yamaguchi et al. |
| 4,935,105 A | 6/1990 | Churchouse |
| 4,938,860 A | 7/1990 | Wogoman |
| 4,970,145 A | 11/1990 | Bennetto et al. |
| 5,049,487 A | 9/1991 | Phillips et al. |
| 5,059,394 A | 10/1991 | Phillips et al. |
| 5,066,372 A | 11/1991 | Wetall |
| 5,120,420 A | 6/1992 | Nankai et al. |
| 5,122,244 A | 6/1992 | Hoenes et al. |
| 5,141,850 A | 8/1992 | Cole et al. |
| 5,141,868 A | 8/1992 | Shanks et al. |
| 5,143,694 A | 9/1992 | Schafer et al. |
| 5,179,005 A | 1/1993 | Phillips et al. |
| 5,187,100 A | 2/1993 | Matzinger et al. |
| 5,192,415 A | 3/1993 | Yoshioka et al. |
| 5,243,516 A | 9/1993 | White |
| 5,250,439 A | 10/1993 | Musho et al. |
| 5,264,103 A | 11/1993 | Yoshioka et al. |
| 5,266,179 A | 11/1993 | Nankai et al. |
| 5,281,395 A | 1/1994 | Markart et al. |
| 5,286,362 A | 2/1994 | Hoenes et al. |
| 5,288,636 A | 2/1994 | Pollmann et al. |
| 5,296,192 A | 3/1994 | Carroll et al. |
| 5,304,468 A | 4/1994 | Phillips et al. |
| 5,306,623 A | 4/1994 | Kiser et al. |
| 5,344,754 A | 9/1994 | Zweig |
| 5,366,609 A | 11/1994 | White et al. |
| 5,379,214 A | 1/1995 | Arbuckle et al. |
| 5,384,028 A | 1/1995 | Ito |
| 5,385,846 A | 1/1995 | Kuhn et al. |
| 5,389,215 A | 2/1995 | Horiuchi et al. |
| 5,395,504 A | 3/1995 | Saurer et al. |
| 5,413,690 A | 5/1995 | Kost et al. |
| 5,413,764 A | 5/1995 | Haar |
| 5,418,142 A | 5/1995 | Kiser et al. |
| 5,421,189 A | 6/1995 | Dussault |
| 5,424,035 A | 6/1995 | Hones et al. |
| 5,426,032 A | 6/1995 | Phillips et al. |
| 5,437,999 A | 8/1995 | Diebold et al. |
| 5,438,271 A | 8/1995 | White et al. |
| 5,439,826 A | 8/1995 | Kontorovich |
| 5,469,846 A | 11/1995 | Khan |
| 5,470,533 A | 11/1995 | Shindo et al. |
| 5,494,638 A | 2/1996 | Gullick |
| 5,508,171 A | 4/1996 | Walling et al. |
| 5,509,410 A | 4/1996 | Hill et al. |
| 5,515,170 A | 5/1996 | Matzinger et al. |
| 5,526,120 A | 6/1996 | Jina et al. |
| 5,547,702 A | 8/1996 | Gleisner |
| 5,552,116 A | 9/1996 | Yokota et al. |
| 5,554,531 A | 9/1996 | Zweig |
| 5,563,042 A | 10/1996 | Phillips et al. |
| 5,569,608 A | 10/1996 | Sommer |
| 5,575,895 A | 11/1996 | Ikeda et al. |
| 5,575,930 A | 11/1996 | Tetje-Girault et al. |
| 5,580,794 A | 12/1996 | Allen |
| 5,582,697 A | 12/1996 | Ikeda et al. |
| 5,597,532 A | 1/1997 | Connolly |
| 5,605,837 A | 2/1997 | Karimi et al. |
| 5,620,579 A | 4/1997 | Genshaw et al. |
| 5,620,863 A | 4/1997 | Tomasco et al. |
| 5,627,075 A | 5/1997 | Bateson |
| 5,628,890 A | 5/1997 | Carter et al. |
| 5,645,798 A | 7/1997 | Schreiber et al. |
| 5,650,062 A | 7/1997 | Ikeda et al. |
| 5,653,863 A | 8/1997 | Genshaw et al. |
| 5,656,502 A | 8/1997 | MacKay et al. |
| 5,658,443 A | 8/1997 | Yamamoto et al. |
| 5,665,215 A | 9/1997 | Bussmann et al. |
| 5,670,031 A | 9/1997 | Hintsche et al. |
| 5,677,546 A | 10/1997 | Yu |
| 5,682,884 A | 11/1997 | Hill et al. |
| 5,691,486 A | 11/1997 | Behringer et al. |
| 5,695,623 A | 12/1997 | Michel et al. |
| 5,698,083 A | 12/1997 | Glass |
| 5,708,247 A | 1/1998 | McAleer et al. |
| 5,720,862 A | 2/1998 | Hamamoto et al. |
| 5,723,284 A | 3/1998 | Ye |
| 5,727,548 A | 3/1998 | Hill et al. |
| 5,757,666 A | 5/1998 | Schreiber et al. |
| 5,762,770 A | 6/1998 | Pritchard et al. |
| 5,766,789 A | 6/1998 | James et al. |
| 5,780,304 A | 7/1998 | Matzinger et al. |
| 5,788,833 A | 8/1998 | Lewis et al. |
| 5,789,255 A | 8/1998 | Yu |
| 5,798,031 A | 8/1998 | Charlton et al. |
| 5,830,341 A | 11/1998 | Gilmartin |
| 5,843,691 A | 12/1998 | Douglas et al. |
| 5,846,744 A | 12/1998 | Athey et al. |
| 5,849,174 A | 12/1998 | Sanghera et al. |
| 5,856,195 A | 1/1999 | Charlton et al. |
| 5,869,972 A | 2/1999 | Birch et al. |
| 5,890,489 A | 4/1999 | Elden |
| 5,897,522 A | 4/1999 | Nitzan |
| 5,904,898 A | 5/1999 | Markart |
| 5,911,872 A | 6/1999 | Lewis et al. |
| 5,916,156 A | 6/1999 | Hildenbrand et al. |
| 5,921,925 A | 7/1999 | Cartmell et al. |
| 5,945,341 A | 8/1999 | Howard, III |
| 5,951,836 A | 9/1999 | McAleer et al. |
| 5,965,380 A | 10/1999 | Heller et al. |
| 5,968,760 A | 10/1999 | Phillips et al. |
| 5,989,917 A | 11/1999 | McAleer et al. |
| 5,997,817 A | 12/1999 | Crismore et al. |
| 6,004,441 A | 12/1999 | Fujiwara et al. |
| 6,036,919 A | 3/2000 | Thym et al. |
| 6,044,285 A | 3/2000 | Chaiken et al. |
| 6,071,391 A | 6/2000 | Gotoh et al. |
| 6,087,182 A | 7/2000 | Jeng et al. |
| 6,091,975 A | 7/2000 | Daddona et al. |
| 6,102,872 A | 8/2000 | Doneen et al. |
| 6,103,033 A | 8/2000 | Say et al. |
| 6,120,676 A | 9/2000 | Heller et al. |
| 6,121,009 A | 9/2000 | Heller et al. |
| 6,121,050 A | 9/2000 | Han |
| 6,129,823 A | 10/2000 | Hughes et al. |
| 6,134,461 A | 10/2000 | Say et al. |
| 6,143,164 A | 11/2000 | Heller et al. |
| 6,144,869 A | 11/2000 | Berner et al. |
| 6,150,124 A | 11/2000 | Riedel |
| 6,153,069 A | 11/2000 | Pottgen et al. |
| RE36,991 E | 12/2000 | Yamamoto et al. |
| 6,156,173 A | 12/2000 | Gotah et al. |
| 6,159,745 A | 12/2000 | Roberts et al. |
| 6,162,611 A | 12/2000 | Heller et al. |
| 6,162,639 A | 12/2000 | Douglas |
| 6,168,957 B1 | 1/2001 | Matzinger et al. |
| 6,170,318 B1 | 1/2001 | Lewis |
| 6,174,420 B1 | 1/2001 | Hodges et al. |
| 6,175,752 B1 | 1/2001 | Say et al. |
| 6,176,988 B1 | 1/2001 | Kessler |
| 6,179,979 B1 | 1/2001 | Hodges et al. |
| 6,180,062 B1 | 1/2001 | Naka et al. |
| 6,193,873 B1 | 2/2001 | Ohara et al. |
| 6,200,773 B1 | 3/2001 | Ouyang et al. |
| 6,225,078 B1 | 5/2001 | Ikeda et al. |
| 6,241,862 B1 | 6/2001 | McAleer et al. |
| 6,251,260 B1 | 6/2001 | Heller et al. |
| 6,258,229 B1 | 7/2001 | Winarta et al. |

| | | |
|---|---|---|
| 6,258,254 B1 | 7/2001 | Miyamoto et al. |
| 6,259,937 B1 | 7/2001 | Schulman et al. |
| 6,268,162 B1 | 7/2001 | Phillips et al. |
| 6,270,637 B1 | 8/2001 | Crismore et al. |
| 6,271,044 B1 | 8/2001 | Ballerstadt et al. |
| 6,277,641 B1 | 8/2001 | Yager |
| 6,281,006 B1 | 8/2001 | Heller et al. |
| 6,284,125 B1 | 9/2001 | Hodges et al. |
| 6,284,550 B1 | 9/2001 | Carroll et al. |
| 6,287,451 B1 | 9/2001 | Winarta et al. |
| 6,287,595 B1 | 9/2001 | Loewy et al. |
| 6,295,506 B1 | 9/2001 | Heinonen et al. |
| 6,299,757 B1 | 10/2001 | Feldman et al. |
| 6,300,123 B1 | 10/2001 | Vadgama et al. |
| 6,300,142 B1 | 10/2001 | Andrewes et al. |
| 6,309,526 B1 | 10/2001 | Fujiwara et al. |
| 6,315,951 B1 | 11/2001 | Markart |
| 6,316,264 B1 | 11/2001 | Corey et al. |
| 6,325,917 B1 | 12/2001 | Maxwell et al. |
| 6,329,161 B1 | 12/2001 | Heller et al. |
| 6,335,203 B1 | 1/2002 | Patel et al. |
| 6,338,790 B1 | 1/2002 | Feldman et al. |
| 6,340,428 B1 | 1/2002 | Ikeda et al. |
| 6,349,230 B1 | 2/2002 | Kawanaka |
| 6,377,894 B1 | 4/2002 | Deweese et al. |
| 6,377,896 B1 | 4/2002 | Sato et al. |
| 6,379,513 B1 | 4/2002 | Chambers et al. |
| 6,395,227 B1 | 5/2002 | Kiser et al. |
| 6,413,395 B1 | 7/2002 | Bhullar et al. |
| 6,413,410 B1 | 7/2002 | Hodges et al. |
| 6,420,128 B1 | 7/2002 | Ouyang et al. |
| 6,444,115 B1 | 9/2002 | Hodges et al. |
| 6,447,657 B1 | 9/2002 | Bhullar et al. |
| 6,454,921 B1 | 9/2002 | Hodges et al. |
| 6,458,258 B2 | 10/2002 | Taniike et al. |
| 6,461,496 B1 | 10/2002 | Feldman et al. |
| 6,475,360 B1 | 11/2002 | Hodges et al. |
| 6,475,372 B1 | 11/2002 | Ohara et al. |
| 6,484,046 B1 | 11/2002 | Say et al. |
| 6,485,923 B1 | 11/2002 | Yani et al. |
| 6,488,827 B1 | 12/2002 | Shartle |
| 6,489,133 B2 | 12/2002 | Phillips et al. |
| 6,491,803 B1 | 12/2002 | Shen et al. |
| 6,491,870 B2 | 12/2002 | Patel et al. |
| 6,501,976 B1 | 12/2002 | Sohrab |
| 6,503,381 B1 | 1/2003 | Gotoh et al. |
| 6,514,718 B2 | 2/2003 | Heller et al. |
| 6,514,769 B2 | 2/2003 | Lee |
| 6,521,110 B1 | 2/2003 | Hodges et al. |
| 6,521,182 B1 | 2/2003 | Shartle et al. |
| 6,525,330 B2 | 2/2003 | Paolini et al. |
| 6,525,549 B1 | 2/2003 | Poellmann |
| 6,526,298 B1 | 2/2003 | Khalil et al. |
| 6,531,040 B2 | 3/2003 | Musho et al. |
| 6,531,322 B1 | 3/2003 | Jurik et al. |
| 6,540,890 B1 | 4/2003 | Bhullar et al. |
| 6,540,891 B1 | 4/2003 | Stewart et al. |
| 6,541,266 B2 | 4/2003 | Modzelewski et al. |
| 6,544,474 B2 | 4/2003 | Douglas |
| 6,549,796 B2 | 4/2003 | Schrab |
| 6,551,494 B1 | 4/2003 | Heller et al. |
| 6,555,061 B1 | 4/2003 | Leong et al. |
| 6,558,528 B1 | 5/2003 | Matzinger |
| 6,560,471 B1 | 5/2003 | Heller et al. |
| 6,561,989 B2 | 5/2003 | Whitson |
| 6,565,509 B1 | 5/2003 | Say et al. |
| 6,565,738 B1 | 5/2003 | Henning et al. |
| 6,571,651 B1 | 6/2003 | Hodges |
| 6,572,822 B2 | 6/2003 | Jurik et al. |
| 6,576,101 B1 | 6/2003 | Heller et al. |
| 6,576,117 B1 | 6/2003 | Iketaki et al. |
| 6,576,416 B2 | 6/2003 | Haviland et al. |
| 6,576,461 B2 | 6/2003 | Heller et al. |
| 6,579,690 B1 | 6/2003 | Bonnecaze et al. |
| 6,591,125 B1 | 7/2003 | Buse et al. |
| 6,592,745 B1 | 7/2003 | Feldman et al. |
| 6,594,514 B2 | 7/2003 | Berner et al. |
| 6,599,406 B1 | 7/2003 | Kawanaka et al. |
| 6,599,407 B2 | 7/2003 | Taniike et al. |
| 6,600,997 B2 | 7/2003 | Deweese et al. |
| 6,605,200 B1 | 8/2003 | Mao et al. |
| 6,605,201 B1 | 8/2003 | Mao et al. |
| 6,607,658 B1 | 8/2003 | Heller et al. |
| 6,616,819 B1 | 9/2003 | Liamos et al. |
| 6,618,603 B2 | 9/2003 | Yaralli et al. |
| 6,618,934 B1 | 9/2003 | Feldman et al. |
| 6,627,057 B1 | 9/2003 | Bhullar et al. |
| 6,632,349 B1 | 10/2003 | Hodges et al. |
| 6,638,415 B1 | 10/2003 | Hodges et al. |
| 6,638,716 B2 | 10/2003 | Heller et al. |
| 6,645,359 B1 | 11/2003 | Bhullar et al. |
| 6,654,625 B1 | 11/2003 | Say et al. |
| 6,656,702 B1 | 12/2003 | Yugawa et al. |
| 6,676,995 B2 | 1/2004 | Dick et al. |
| 6,689,411 B2 | 2/2004 | Dick et al. |
| 6,716,620 B2 | 4/2004 | Bashir et al. |
| 6,719,887 B2 | 4/2004 | Hasegawa et al. |
| 6,723,371 B2 | 4/2004 | Chih-Lui |
| 6,743,635 B2 | 6/2004 | Neel et al. |
| 6,746,582 B2 | 6/2004 | Heller et al. |
| 6,749,740 B2 | 6/2004 | Liamos et al. |
| 6,764,581 B1 | 7/2004 | Forrow et al. |
| 6,776,888 B2 | 8/2004 | Yamamoto et al. |
| 6,777,243 B2 | 8/2004 | Fukuoka et al. |
| 6,787,013 B2 | 9/2004 | Chang et al. |
| 6,800,488 B2 | 10/2004 | Khan et al. |
| 6,814,844 B2 | 11/2004 | Bhullar et al. |
| 6,818,180 B2 | 11/2004 | Douglas |
| 6,821,483 B2 | 11/2004 | Phillips et al. |
| 6,827,829 B2 | 12/2004 | Kawanaka et al. |
| 6,830,669 B2 | 12/2004 | Miyazaki et al. |
| 6,833,110 B2 | 12/2004 | Black |
| 6,841,389 B2 | 1/2005 | Novikov et al. |
| 6,856,125 B2 | 2/2005 | Kermani |
| 6,860,978 B2 | 3/2005 | Yamanishi et al. |
| 6,863,800 B2 | 3/2005 | Karinka |
| 6,881,322 B2 | 4/2005 | Tokunaga et al. |
| 6,881,550 B2 | 4/2005 | Phillips et al. |
| 6,881,551 B2 | 4/2005 | Heller |
| 7,022,218 B2 | 4/2006 | Taniike et al. |
| 7,041,206 B2 | 5/2006 | Gephart et al. |
| 2001/0042683 A1 | 11/2001 | Musho et al. |
| 2001/0052470 A1 | 12/2001 | Hodges et al. |
| 2001/0053535 A1 | 12/2001 | Bashir et al. |
| 2001/0054319 A1 | 12/2001 | Heller et al. |
| 2001/0055784 A1 | 12/2001 | Noda et al. |
| 2002/0004196 A1 | 1/2002 | Whitson |
| 2002/0019707 A1 | 2/2002 | Cohen et al. |
| 2002/0043471 A1 | 4/2002 | Ikeda et al. |
| 2002/0044890 A1 | 4/2002 | Black |
| 2002/0053523 A1 | 5/2002 | Liamos et al. |
| 2002/0081588 A1 | 6/2002 | De Lumley-woodyear et al. |
| 2002/0082797 A1 | 6/2002 | Deweese et al. |
| 2002/0084196 A1 | 7/2002 | Liamos et al. |
| 2002/0092612 A1 | 7/2002 | Davies et al. |
| 2002/0100685 A1 | 8/2002 | Huang et al. |
| 2002/0102739 A1 | 8/2002 | Nomura et al. |
| 2002/0112969 A1 | 8/2002 | Hodges et al. |
| 2002/0125145 A1 | 9/2002 | Ohara et al. |
| 2002/0133064 A1 | 9/2002 | Ueno et al. |
| 2002/0137200 A1 | 9/2002 | Takahashi et al. |
| 2002/0137230 A1 | 9/2002 | Nadaoka et al. |
| 2002/0139692 A1 | 10/2002 | Tokunaga et al. |
| 2002/0148739 A2 | 10/2002 | Liamos et al. |
| 2002/0157948 A2 | 10/2002 | Liamos et al. |
| 2002/0164822 A1 | 11/2002 | Takahashi et al. |

| | | | | | |
|---|---|---|---|---|---|
| 2002/0168290 A1 | 11/2002 | Yuzhakov et al. | EP | 0 164 180 B2 | 12/1985 |
| 2002/0170823 A1 | 11/2002 | Housefield et al. | EP | 0 170 375 A2 | 2/1986 |
| 2002/0175087 A1 | 11/2002 | Hodges et al. | EP | 0 171 148 B1 | 2/1986 |
| 2002/0177788 A1 | 11/2002 | Hodges et al. | EP | 0 186 286 B1 | 7/1986 |
| 2002/0179440 A1 | 12/2002 | Tokunaga et al. | EP | 0 230 472 B1 | 8/1987 |
| 2002/0179442 A1 | 12/2002 | Miyazaki et al. | EP | 0 255 291 B1 | 2/1988 |
| 2002/0185385 A1 | 12/2002 | Charlton | EP | 0 267 724 A | 5/1988 |
| 2002/0189941 A1 | 12/2002 | Katsuki | EP | 0 287 883 A1 | 10/1988 |
| 2003/0000834 A1 | 1/2003 | Yoshioka et al. | EP | 0 359 831 B1 | 3/1990 |
| 2003/0004403 A1 | 1/2003 | Drinan et al. | EP | 0 383 322 B1 | 8/1990 |
| 2003/0024811 A1 | 2/2003 | Davies et al. | EP | 0 471 986 A | 2/1992 |
| 2003/0032875 A1 | 2/2003 | Taniike et al. | EP | 0 537 761 A2 | 4/1993 |
| 2003/0042137 A1 | 3/2003 | Mao et al. | EP | 0 546 536 B1 | 6/1993 |
| 2003/0042150 A1 | 3/2003 | Ryu et al. | EP | 0 732 406 A1 | 9/1996 |
| 2003/0046811 A1 | 3/2003 | Chang et al. | EP | 0 736 607 A1 | 10/1996 |
| 2003/0073152 A1 | 4/2003 | Phillips et al. | EP | 0 740 786 B1 | 11/1996 |
| 2003/0073153 A1 | 4/2003 | Phillips et al. | EP | 0 837 320 A3 | 4/1998 |
| 2003/0088166 A1 | 5/2003 | Say et al. | EP | 0 840 122 A2 | 5/1998 |
| 2003/0094383 A1 | 5/2003 | Kermani | EP | 0 851 224 B1 | 7/1998 |
| 2003/0097981 A1 | 5/2003 | Dick et al. | EP | 0 873 514 B1 | 10/1998 |
| 2003/0098233 A1 | 5/2003 | Kermani et al. | EP | 0 876 506 B1 | 11/1998 |
| 2003/0099773 A1 | 5/2003 | Dick et al. | EP | 0 882 226 B1 | 12/1998 |
| 2003/0100030 A1 | 5/2003 | Nadaoka et al. | EP | 0 887 421 A1 | 12/1998 |
| 2003/0102213 A1 | 6/2003 | Gotoh et al. | EP | 0 958 495 B1 | 11/1999 |
| 2003/0106809 A1 | 6/2003 | Kermani et al. | EP | 0 964 059 A2 | 12/1999 |
| 2003/0109798 A1 | 6/2003 | Kermani | EP | 0 967 480 B1 | 12/1999 |
| 2003/0132110 A1 | 7/2003 | Hasegawa et al. | EP | 0 987 544 A1 | 3/2000 |
| 2003/0143113 A2 | 7/2003 | Yuzhakov et al. | EP | 1 009 850 B1 | 6/2000 |
| 2003/0146110 A1 | 8/2003 | Karinka et al. | EP | 1 024 358 A1 | 8/2000 |
| 2003/0146436 A1 | 8/2003 | Parker et al. | EP | 1 074 832 A1 | 2/2001 |
| 2003/0150724 A1 | 8/2003 | Kawanaka et al. | EP | 1 102 991 B1 | 5/2001 |
| 2003/0155237 A1 | 8/2003 | Surridge et al. | EP | 1 119 637 B1 | 8/2001 |
| 2003/0159944 A1 | 8/2003 | Pottgen et al. | EP | 1 129 211 B1 | 9/2001 |
| 2003/0159945 A1 | 8/2003 | Miyazaki et al. | EP | 1 130 390 A1 | 9/2001 |
| 2003/0164293 A1 | 9/2003 | Hodges et al. | EP | 1 152 239 A1 | 11/2001 |
| 2003/0175841 A1 | 9/2003 | Watanabe et al. | EP | 1 156 324 A1 | 11/2001 |
| 2003/0175946 A1 | 9/2003 | Tokunaga et al. | EP | 1 225 448 A2 | 7/2002 |
| 2003/0176183 A1 | 9/2003 | Drucker et al. | EP | 1 235 069 A1 | 8/2002 |
| 2003/0180183 A1 | 9/2003 | Fukuoka et al. | EP | 1 236 995 A1 | 9/2002 |
| 2003/0185705 A1 | 10/2003 | Otake | EP | 1 256 798 A1 | 11/2002 |
| 2003/0187338 A1 | 10/2003 | Say et al. | EP | 1 260 589 A2 | 11/2002 |
| 2003/0188427 A1 | 10/2003 | Say et al. | EP | 1 275 732 A1 | 1/2003 |
| 2003/0199744 A1 | 10/2003 | Buse et al. | EP | 1 281 955 A1 | 2/2003 |
| 2003/0199893 A1 | 10/2003 | Boecker et al. | EP | 1 288 654 A1 | 3/2003 |
| 2003/0201194 A1 | 10/2003 | Heller et al. | EP | 1 308 720 A1 | 5/2003 |
| 2003/0203498 A1 | 10/2003 | Neel et al. | EP | 1 312 919 A2 | 5/2003 |
| 2003/0203503 A1 | 10/2003 | Fukuoka et al. | EP | 1 316 367 A | 6/2003 |
| 2003/0217918 A1 | 11/2003 | Davies et al. | EP | 1 318 396 A1 | 6/2003 |
| 2004/0005721 A1 | 1/2004 | Tanike et al. | EP | 1 324 025 A2 | 7/2003 |
| 2004/0016642 A1 | 1/2004 | Miyazaki et al. | EP | 1 327 881 A1 | 7/2003 |
| 2004/0020777 A1 | 2/2004 | Miyamoto et al. | EP | 1 352 611 A1 | 10/2003 |
| 2004/0067166 A1 | 4/2004 | Karinka et al. | EP | 1 352 969 A1 | 10/2003 |
| 2004/0094432 A1 | 5/2004 | Neel et al. | EP | 1 369 684 A1 | 12/2003 |
| 2004/0094433 A1 | 5/2004 | Neel et al. | EP | 1 369 687 A1 | 12/2003 |
| 2004/0096928 A1 | 5/2004 | Hasegawa et al. | EP | 1 391 716 A2 | 2/2004 |
| 2004/0099540 A1 | 5/2004 | Neel et al. | EP | 1 394 535 A1 | 3/2004 |
| 2004/0104131 A1 | 6/2004 | Neel et al. | EP | 1 431 758 A | 6/2004 |
| 2004/0106941 A1 | 6/2004 | Roe et al. | GB | 2365123 A | 2/2002 |
| 2004/0127818 A1 | 7/2004 | Roe et al. | JP | 63128252 A2 | 5/1988 |
| 2004/0127819 A1 | 7/2004 | Roe et al. | JP | 1291153 A2 | 11/1989 |
| 2004/0182703 A1 | 9/2004 | Bell et al. | JP | 05-312761 | 11/1993 |
| 2004/0206625 A1 | 10/2004 | Bhullar et al. | JP | 09-189675 | 7/1997 |
| 2004/0251131 A1 | 12/2004 | Ueno et al. | JP | 10 307119 A | 11/1998 |
| 2005/0013731 A1 | 1/2005 | Burke et al. | JP | 11 337514 A | 12/1999 |
| 2005/0016844 A1 | 1/2005 | Burke et al. | JP | 2004-20465 | 1/2004 |
| 2005/0019212 A1 | 1/2005 | Bhullar et al. | WO | WO 86/07632 | 12/1986 |
| | | | WO | WO 89/09397 | 10/1989 |
| | FOREIGN PATENT DOCUMENTS | | WO | WO 92/22669 | 12/1992 |
| | | | WO | WO 94/16095 | 7/1994 |
| DE | 102 22 428 A | 12/2002 | WO | WO 94/28414 | 12/1994 |
| EP | 0 057 110 B2 | 8/1982 | WO | WO 94/29705 | 12/1994 |
| EP | 0 127 958 B2 | 12/1984 | WO | WO 95/22597 | 8/1995 |
| EP | 0 034 049 B1 | 1/1985 | WO | WO 96/07908 | 3/1996 |

| | | |
|---|---|---|
| WO | WO 96/15454 | 5/1996 |
| WO | WO 96/33403 | 10/1996 |
| WO | WO 97/02487 | 1/1997 |
| WO | WO 97/29847 | 8/1997 |
| WO | WO 97/30344 | 8/1997 |
| WO | WO 97/34140 A | 9/1997 |
| WO | WO 97/39343 | 10/1997 |
| WO | WO 97/45719 | 12/1997 |
| WO | WO 98/30904 A | 7/1998 |
| WO | WO 98/35225 | 8/1998 |
| WO | WO 98/55853 | 12/1998 |
| WO | WO 99/05516 | 2/1999 |
| WO | WO 99/13099 | 3/1999 |
| WO | WO 99/13100 | 3/1999 |
| WO | WO 99/30152 | 6/1999 |
| WO | WO 99/32881 | 7/1999 |
| WO | WO 99/39627 | 8/1999 |
| WO | WO 99/45387 | 9/1999 |
| WO | WO 99/51974 | 10/1999 |
| WO | WO 99/58709 | 11/1999 |
| WO | WO 99/64620 | 12/1999 |
| WO | WO 00/10007 | 2/2000 |
| WO | WO 00/18294 A | 4/2000 |
| WO | WO 00/20626 | 4/2000 |
| WO | WO 00/26638 | 5/2000 |
| WO | WO 00/28068 | 5/2000 |
| WO | WO 00/33063 A | 6/2000 |
| WO | WO 00/33072 | 6/2000 |
| WO | WO 00/33074 | 6/2000 |
| WO | WO 00/42422 | 7/2000 |
| WO | WO 00/60340 | 10/2000 |
| WO | WO 00/62047 | 10/2000 |
| WO | WO 00/73778 A1 | 12/2000 |
| WO | WO 00/73785 A2 | 12/2000 |
| WO | WO 00/78992 A2 | 12/2000 |
| WO | WO 01/25775 A1 | 4/2001 |
| WO | WO 01/25776 A1 | 4/2001 |
| WO | WO 01/33216 A1 | 5/2001 |
| WO | WO 01/36953 A1 | 5/2001 |
| WO | WO 01/40788 A1 | 6/2001 |
| WO | WO 01/46457 A2 | 6/2001 |
| WO | WO 01/57238 A2 | 8/2001 |
| WO | WO 01/57239 A2 | 8/2001 |
| WO | WO 01/57510 A2 | 8/2001 |
| WO | WO 01/67099 A1 | 9/2001 |
| WO | WO 01/71328 A1 | 9/2001 |
| WO | WO 01/71329 A1 | 9/2001 |
| WO | WO 01/72220 A1 | 10/2001 |
| WO | WO 01/73109 A2 | 10/2001 |
| WO | WO 01/73114 A2 | 10/2001 |
| WO | WO 01/73124 A2 | 10/2001 |
| WO | WO 01/73419 A1 | 10/2001 |
| WO | WO 01/73420 A1 | 10/2001 |
| WO | WO 01/75438 A2 | 10/2001 |
| WO | WO 01/84133 A1 | 11/2001 |
| WO | WO 02/00112 A2 | 1/2002 |
| WO | WO 02/08250 A1 | 1/2002 |
| WO | WO 02/08753 A2 | 1/2002 |
| WO | WO 02/10728 A1 | 2/2002 |
| WO | WO 02/14535 A2 | 2/2002 |
| WO | WO 02/22855 A2 | 3/2002 |
| WO | WO 02/32559 A | 4/2002 |
| WO | WO 02/49507 A1 | 6/2002 |
| WO | WO 02/50609 A2 | 6/2002 |
| WO | WO 02/054055 A1 | 7/2002 |
| WO | WO 02/057767 A1 | 7/2002 |
| WO | WO 02/057768 A1 | 7/2002 |
| WO | WO 02/057781 A2 | 7/2002 |
| WO | WO 02/058537 A2 | 8/2002 |
| WO | WO 02/067768 A2 | 8/2002 |
| WO | WO 02/070734 A1 | 9/2002 |
| WO | WO 02/071044 A1 | 9/2002 |
| WO | WO 02/078512 A2 | 10/2002 |
| WO | WO 02/078533 A2 | 10/2002 |
| WO | WO 02/086483 A1 | 10/2002 |
| WO | WO 02/097418 A1 | 12/2002 |
| WO | WO 02/103343 A1 | 12/2002 |
| WO | WO 03/005015 A1 | 1/2003 |
| WO | WO 03/012422 A1 | 2/2003 |
| WO | WO 03/014740 A1 | 2/2003 |
| WO | WO 03/014741 A1 | 2/2003 |
| WO | WO 03/029804 A | 4/2003 |
| WO | WO 03/032411 A2 | 4/2003 |
| WO | WO 03/042679 A1 | 5/2003 |
| WO | WO 03/042680 A1 | 5/2003 |
| WO | WO 03/043945 A | 5/2003 |
| WO | WO 03/044511 A2 | 5/2003 |
| WO | WO 03/048756 A1 | 6/2003 |
| WO | WO 03/056345 A1 | 7/2003 |
| WO | WO 03/060154 A2 | 7/2003 |
| WO | WO 03/067252 A2 | 8/2003 |
| WO | WO 03/069304 A2 | 8/2003 |
| WO | WO 03/083469 A2 | 10/2003 |
| WO | WO 03/085372 A2 | 10/2003 |
| WO | WO 03/091717 A | 11/2003 |
| WO | WO 2004/005908 A1 | 1/2004 |
| WO | WO 2004/034053 A2 | 4/2004 |
| WO | WO 2004/113901 A1 | 12/2004 |
| WO | WO 2004/113902 A1 | 12/2004 |

OTHER PUBLICATIONS

Japanese Patent Application No. 517450/2006 Office Action mailed Dec. 15, 2009.

"Verarbeitung von Dispersionshaftlebstoffen", 1022 Adhasion, 37 Dec. 1993, No. 12, Muchen, DE.

Brian A. Gregg et al., "Cross-Linked Redox Gels Containing Glucose Oxidase for Amperometric Biosensor Applications", Analytical Chemistry, Feb. 1, 1990, pp. 258-263, vol. 62, No. 3.

Cosimino Malitesta et al., "Glucose Fast-Response Amperometric Sensor Based on Glucose Oxidase Immobilized in an Electropolymerized Poly (o-phenylenediamine) Film", Analytical Chemistry, Dec. 15, 1990, pp. 2735-2740, vol. 62, No. 24.

David L. Williams et al., "Electrochemical-Enzymatic Analysis of Blood Glucose and Lactate", Analytical Chemistry, January 1970, pp. 118-121, vol. 42, No. 1.

Koichi Aoki, "Quantitative analysis of reversible diffusion-controlled currents of redox soluble species at interdigitated array electrodes under steady-state conditions", Journal of Electroanalytical Chemistry, pp. 269-282, issue/volume vol. 256, No. 2, Elsevier Sequoia S.A., Lausanne.

Koichi Aoki, "Theory of the steady-state current of a redox couple at interdigitated array electrodes of which pairs are insulated electrically by steps", Journal of Electroanalytical Chemistry, Oct. 10, 1989, pp. 35-41, vol. 270.

Leonard M. Tender et al., "Electrochemical Patterning of Self-Assembled Monolayers onto Microscopic Arrays of Gold Electrodes Fabricated by Laser Ablation", Langmuir, pp. 5515-5518 (1996), vol. 12, No. 23.

M. Beyer et al., "Development and application of a new enzyme sensor type based on the EIS-capacitance structure for bioprocess control", Biosensors & Bioelectronics, 1994, pp. 17-21.

Matsuhiko Nishizawa et al., "Penicillin Sensor Based on a Microarray Electrode Coated with pH-responsive Polypyrrole", Analytical Chemistry, Nov. 1, 1992, pp. 2642-2644, vol. 64, No. 21.

N.A. Morris et al., "An Electrochemical Capillary Fill Device for the Analysis of Glucose Incorporating Glucose Oxidase and Ruthenium (III) Hexamine as Mediator", Electroanalysis, 1992, pp. 1-9, vol. 4.

Osamu Niwa, "Fabrication and characteristics of vertically separated interdigitated array electrodes", Journal of Electroanalytical Chemistry, Aug. 10, 1989, pp. 291-297, vol. 267.

Richard F. Taylor et al., "An Acetylcholine Receptor-Based Biosensor For The Detection of Cholinergic Agents", Analytica Chimica Acta, 1988, pp. 131-138.

T. Boltshauser et al., "Capacitive Humidity Sensors in SACMOS Technology with Moisture Absorbing Photosensitive Polyimide", Sensors and Actuators, 1991, pp. 509-512.

Tsutomu Horiuchi et al., "Limiting Current Enhancement by Self-Induced Redox Cycling on a Micro-Macro Twin Electrode", Journal of the Electrochemical Society, Dec. 1991, pp. 3549-3553, vol. 138, No. 12.

Vasile V. Cosofret et al., "Microfabricated Sensor Arrays Sensitive to pH and K+ for Ionic Distribution Measurements in the Beating Heart", Analytical Chemistry, May 15, 1995, pp. 1647-1653, vol. 67, No. 10.

W. Preidel et al., "In vitro measurements with electrocatalytic glucose sensor in blood", Biomed. Biochem. Acta, 1989, pp. 897-903.

Koichi Aoki, "Quantitative analysis of reversible diffusion-controlled currents of redox soluble species at interdigitated array electrodes under steady-state conditions", Journal of Electroanalytical Chemistry, pp. 269-282, issue/volume vol. 256, No. 2, Elsevier Sequoia S.A., Lausanne.

METHOD AND REAGENT FOR PRODUCING NARROW, HOMOGENOUS REAGENT STRIPS

RELATED APPLICATIONS

This application is a divisional of application Ser. No. 10/871,966, filed Jun. 18, 2004, now U.S. Pat. No. 7,749,437 which claims the benefit of U.S. Provisional Application No. 60/480,397, filed Jun. 20, 2003, which are hereby incorporated by reference.

This application is related to commonly assigned U.S. application Ser. No. 10/871,673 entitled "Reagent Stripe for Test Strip" (hereinafter "Reagent Stripe application"), filed on Jun. 18, 2004, which is hereby incorporated by reference.

FIELD OF THE INVENTION

The present invention relates generally to reagents used in biosensors or test strips and more particularly to the production of narrow, homogenous reagent stripes on flat surfaces of test strips.

BACKGROUND AND SUMMARY

Of the numerous methods for applying reagents to test strips, in the past electrochemical biosensors have mainly been produced by using printing techniques such as screen printing processes or dispensing techniques for liquid reagent application and subsequent drying, (see. e.g., U.S. Pat. No. 5,437,999 and WO 97/02487). In connection with so-called "capillary fill" test strips, these dispensing methods have successfully been employed, as in the production of Roche Diagnostics AccuChek® Advantage test strips. While these techniques allow for the production of reliable electrochemical biosensors, they are not well suited for high throughput production lines. In addition, these dispensing techniques suffer from the disadvantage of inhomogeneous drying of the reagent, which leads to non-uniform reagent thickness over the covered electrode area. Also, the above mentioned techniques are not suited for the reliable and reproducible production of extremely thin reagent layers (10 μm or less). Therefore, there exists a need for improved reagent application methods.

Blade coating of reagent compositions onto flat substrates has been suggested and successfully been employed in the production of reagent films coated for example on transparent polymeric substrates (e.g., U.S. Pat. Nos. 5,437,999 and 6,036,919). Usually, films of a width of several centimeters to several meters can be produced by this method. For the production of test strips, the so created reagent layers are cut into small stripes and then applied to the test strip substrate. Blade coating of reagent masses has the disadvantage that—although the center portion of the film is homogenous in thickness—at the edge of the coated area inhomogeneities are found which are believed to be due to drying effects and edge effects. While these inhomogeneities are acceptable if broad bands of reagents are coated onto substrates since the inhomogeneous edge portions of the coating can be discarded by edge trim, these inhomogeneities become more and more unacceptable as the reagent stripe to be coated becomes smaller/narrower.

WO 02/057781 discloses a method for manufacturing reagent strips from web material. Among other things, it discloses that the reagent material may be applied to the strip support material by laying down a narrow stripe of reagent material, which may or may not be supported by a support carrier.

U.S. Patent Application Publication 2003/0097981, U.S. Patent Publication Number 2003/0099773, U.S. Pat. Nos. 6,676,995 and 6,689,411 and EP 1 316 367) disclose a solution stripping system for laying down stripes of reagent solutions on a substrate. The system allows slot-die-coating of reagent solutions to web material, e.g., for electrochemical glucose sensors, which solutions have a low viscosity, from about 0.5 to 25 centipoises (cP=mPa-s).

U.S. Pat. Nos. 3,032,008; 3,886,898; and 4,106,437 teach coating apparatuses useful for coating liquid material onto solid supports.

U.S. Pat. No. 6,036,919 discloses reagent films for optical blood glucose test strips. The reagent composition comprises, among other things, a Xanthan gum.

U.S. Patent Application Publication Number 2003/0146113 discloses reagent films for electrochemical coagulation sensors. The reagent composition comprises, among other things, carboxylated microcrystalline cellulose (Avicel® R591) as a film former.

None of the above-mentioned references satisfies the need for a reliable method for forming narrow (for example, less than 1 cm), thin (for example, less than 10 μm) and homogeneous reagent stripes on solid support material for producing test strips, in particular electrochemical test strips.

It is therefore an object of the invention to provide a method and a corresponding reagent composition with which extremely thin, narrow and homogeneous reagent lines or stripes can be deposited onto flat surfaces, for example, of web material and in particular onto the electrode areas of electrochemical biosensor test strips.

This object is reached by the present invention concerning a reagent for a slot-die-coating process for narrow and homogenous reagent stripes.

In a first aspect, the present invention concerns a reagent composition showing shear thinning, slightly thixotropic or thixotropic behavior.

In a second aspect, the present invention concerns a method of coating the shear thinning, slightly thixotropic or thixotropic reagent composition onto web material using a slot-die-coating process.

In a further aspect, the present invention concerns analytical test elements comprising the shear thinning, slightly thixotropic or thixotropic reagent.

In still another aspect, the present invention concerns reagent compositions that are shear thinning and at least slightly thixotropic. It also concerns analytic test elements and methods for making analytic test elements that include using shear thinning and at least slightly thixotropic reagent compositions.

DESCRIPTION OF THE PREFERRED EMBODIMENTS

Figure 1:
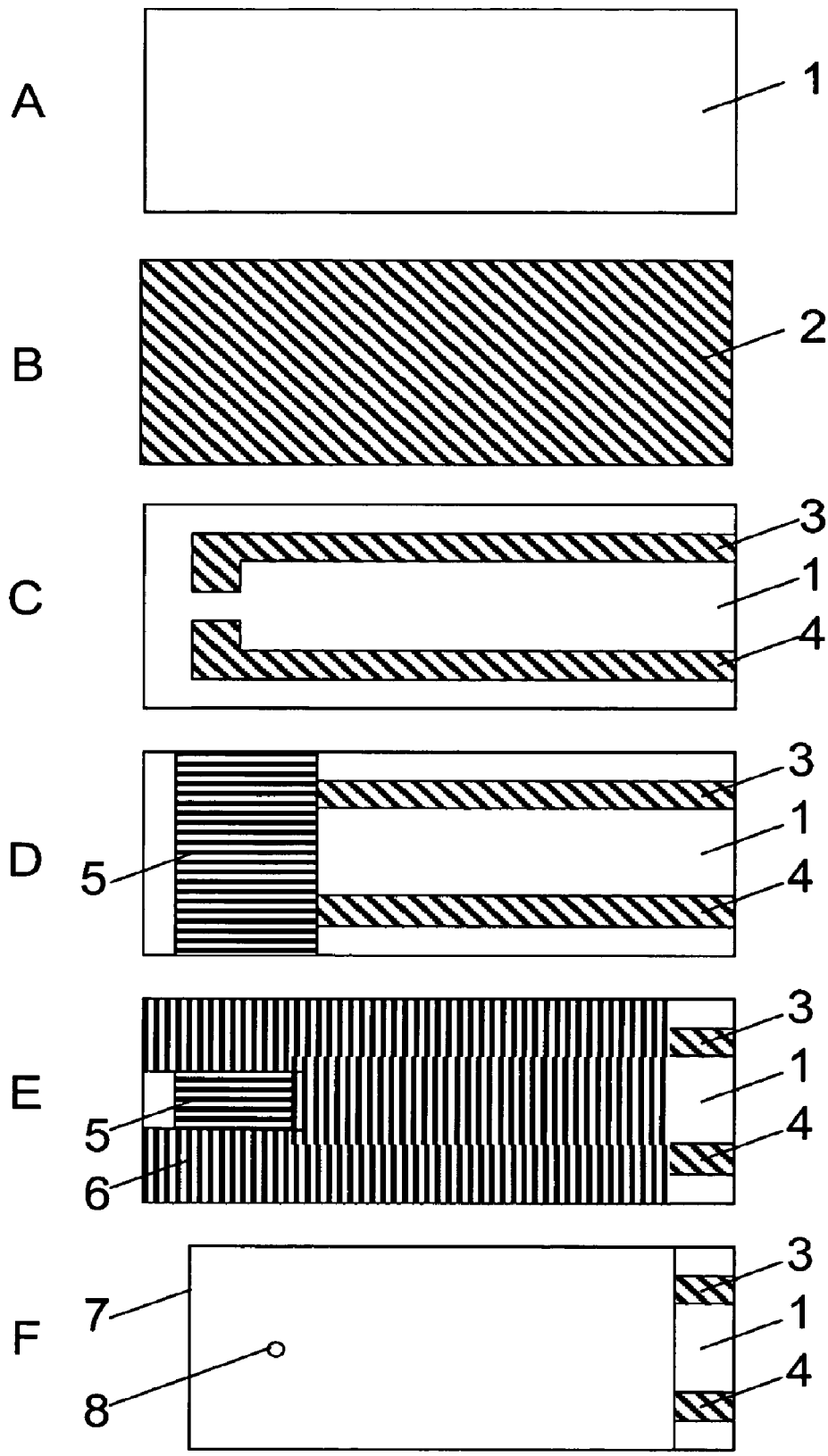
FIG. 1 shows schematically in 6 steps (A-F) how an electrochemical test element with a single reagent zone is manufactured using the slot-die-coating process of the present invention.

For the purposes of promoting an understanding of the principles of the invention, reference will now be made to the specific embodiments illustrated herein and specific language will be used to describe the same. It will nevertheless be understood that no limitation of the scope of the invention is thereby intended. Any alterations and further modifications in the described processes or devices and any further applications of the principles of the invention as described herein, are contemplated as would normally occur to one skilled in the art to which the invention relates. Preferred embodiments of the invention are subject of the dependent claims.

The reagent composition of the present invention is shear thinning, slightly thixotropic or thixotropic. Thixotropic reagent compositions are reagent compositions that show rheologic behavior depending on whether or not external shear force is applied to the reagent composition. Shear thinning reagent compositions are reagent compositions that become thinner, i.e., less viscous, when a shear force is applied to them. In general, before applying a shear force to the reagent composition of the present invention, the composition has a certain viscosity. When a shear force is applied to the composition, its viscosity is reduced. If viscosity increases again—with a certain time-dependency—after the shear force is stopped, the reagent composition shall be regarded as being "shear thinning." If viscosity increases only with a certain delay after the shear force is stopped the reagent composition shall be regarded as being "thixotropic."

Thixotropy is a special case of pseudoplasticity. The thixotropic fluid undergoes "shear thinning." But as shear forces are reduced, viscosity rebuilds and increases at a slower rate, thus producing a hysteresis loop. Slightly thixotropic fluids have a less pronounced hysteresis. In addition, the thixotropic behavior is influenced considerably by the shear history of the material under investigation. In comparative measurements, care should be taken to ensure that an identical or at least very similar history of the samples to be compared is given.

The reagent compositions of the present invention are useful in slot-die-coating processes. During slot-die-coating, the fluid reagent composition is applied to a solid substrate, preferably a substrate in the form of a web material, by forcing the reagent liquid or slurry through the slot of a slot-die-coating head. Usually, the web material passes the slot at a certain distance with certain speed. However, it is also possible that the slot-die-coating head moves across the web material, or that the slot-die head and web both move.

To achieve the objects of the present inventions, it is advantageous that the rheologic properties of the reagent composition used as a coating mass are within certain preferred ranges: The viscosity preferably is between about 70 and about 130 mPa-s, most preferably in the range between 95 and 115 mPa-s. The surface tension ranges advantageously between 30 and 50 mN/m and preferably is about 40±2 mN/m. It is also important that the coating mass shows shear thinning, slightly thixotropic or thixotropic behavior.

One aspect of the present invention is the inclusion of Xanthan gum into the reagent coating mass. One brand of Xanthan gum that can be used is Keltrol®. This component shows an influence on the thixotropy of the reagent mass. Reagent coating masses containing Xanthan gum, for example, Keltrol®, allow the production of extremely thin reagent layers. Preferably, the reagent layer dried films have a thickness less than 10 µm, particularly preferred are dried reagent layers in the range of 1.5 to 5 µm thick.

It has turned out that the incorporation of silica into the reagent compositions of the present invention has an advantageous effect for the viscosity and thixotropy behavior of the reagent. Both properties are enhanced by the addition of silica. Preferably, untreated, hydrophilic silica is used. The particle size of a preferred form of silica ranges from about 1 to 7 µm. It has turned out that silica unexpectedly enhances the thixotropic behavior of other components of the coating mass, in particular of carboxymethyl cellulose and Keltrol®. Also, silica particles in the dry film prevent backside transfer between the coated stripe and the backside of the web, allowing storage of the coated web material as rolls of material. In addition, silica particles in the dry film increase the specific surface of the reagent coating, enabling, for example, rapid dissolving of the reagent in a sample liquid. In capillary fill biosensors comprising reagent stripes including the reagent composition of the present invention, silica also improves capillary fill times and migration of components in the reagent stripe.

Yet another additive for the enhancement of viscosity and thixotropy of the reagent is carboxymethyl cellulose (CMC). Especially preferred embodiments of the inventive reagent composition therefore comprise Xanthan gum, for example, Keltrol®, silica and CMC.

The reagent compositions of the present invention allow the formation of thin reagent layers, for example, the production of electrochemical biosensors. Thin reagent layers have several advantages:

Sample components are in excess compared to the reagent components, therefore not limiting in the determination reactions.

Thin reagent layers can be made homogenous in thickness.

Thin reagent layers contain only small amounts of reagent, which in turn lead to fast reaction times.

The reactions only have short diffusion times.

The thin reagent layers are quickly soluble and therefore lead to quick reagent availability and a rapid equilibration of the matrix after sample rehydration of the reagent stripe, which in turn leads to fast measurements.

The inventive reagent layers can not only be made very thin but also show a high homogeneity down web and across web in the reaction area. The reagent layer in the test area is flat and uniform in thickness. Thickness variations in the coated stripe occur preferably only on the outer 0.2 cm (or less) edges of the stripe. In preferred embodiments, these areas advantageously can either be covered during sensor assembly by spacer layers or can be trimmed from the completed sensor in the final assembly process.

Apart from the above-mentioned components, which influence the rheologic properties of the reagent composition of the present invention, the reagent may further comprise one or more substances (ingredients) of the following substance classes. Substances, additives and ingredients that may be added to the reagent includes, but are not limited to, the following:

buffers, for example, phosphate buffers;

enzymes, such as, glucose dehydrogenase, glucose dye oxidoreductase, glucose oxidase and other oxidases or dehydrogenases such as for lactate or cholesterol determination, esterases etc.;

mediators such as nitrosoanilines, ferricyanide, ruthenium hexamine, osmium complexes;

stabilizers, such as trehalose, sodium succinate;

thickeners, such as Keltrol®, CMC proteins, such as enzymes, bovine serum albumin indicators;

dyes;

surfactants, such as Mega 8®, Geropon®; Triton®, Tween®, Mega 9®, DONS;

film formers, such as Keltrol®, Propiofan®, polyvinyl pyrrolidone, polyvinyl alcohol, Klucel®;

co-factors for enzymes, such as NAD, NADH, PQQ; and silica, for example, DS 300, DS 320, milled silica of DS 300, milled silica of DS 320.

Non-limiting examples of enzymes and mediators that may be used in measuring particular analytes are listed below in Table 1.

Examples of reagent compositions are given as Examples 1, 2, 3 and 4 for electrochemical blood glucose and coagulation sensors, respectively.

In a preferred embodiment, the above reagent compositions are applied to substrates which already contain the electrode traces or circuits of an electrochemical sensor by means of a slot-die-coating process. An example of this process is given in Example 5.

The preferred fabrication technique for these electrode circuits uses a laser ablation process. For a further discussion of laser ablation, please see WO 01/25775, which is hereby incorporated by reference in its entirety. Most preferably, the technique uses a reel-to-reel laser ablation process. This process can be used in reel-to-reel fashion to form extremely thin metal structures on polymeric substrates, which metal struc-

TABLE 1

A partial list of some analytes, enzymes and mediators that can be used to measure the levels of particular analytes.

| Analyte | Enzymes | Mediator (Oxidized Form) | Additional Mediator |
| --- | --- | --- | --- |
| Glucose | Glucose Dehydrogenase and Diaphorase | Ferricyanide | |
| Glucose | Glucose-Dehydrogenase (Quinoprotein) | Ferricyanide | |
| Cholesterol | Cholesterol Esterase and Cholesterol Oxidase | Ferricyanide | 2,6-Dimethyl-1,4-Benzoquinone 2,5-Dichloro-1,4-Benzoquinone or Phenazine Ethosulfate |
| HDL Cholesterol | Cholesterol Esterase and Cholesterol Oxidase | Ferricyanide | 2,6-Dimethyl-1,4-Benzoquinone 2,5-Dichloro-1,4-Benzoquinone or Phenazine Ethosulfate |
| Triglycerides | Lipoprotein Lipase, Glycerol Kinase and Glycerol-3-Phosphate Oxidase | Ferricyanide or Phenazine Ethosulfate | Phenazine Methosulfate |
| Lactate | Lactate Oxidase | Ferricyanide | 2,6-Dichloro-1,4-Benzoquinone |
| Lactate | Lactate Dehydrogenase and Diaphorase | Ferricyanide Phenazine Ethosulfate, or Phenazine Methosulfate | |
| Lactate Dehydrogenase | Diaphorase | Ferricyanide | Phenazine Ethosulfate, or Phenazine Methosulfate |
| Pyruvate | Pyruvate Oxidase | Ferricyanide | |
| Alcohol | Alcohol Oxidase | Phenylenediamine | |
| Bilirubin | Bilirubin Oxidase | 1-Methoxy-Phenazine Methosulfate | |
| Uric Acid | Uricase | Ferricyanide | |

In some of the examples shown in Table 1, at least one additional enzyme is used as a reaction catalyst. Also, some of the examples shown in Table 1 may utilize an additional mediator, which facilitates electron transfer to the oxidised form of the mediator. The additional mediator may be provided to the reagent in lesser amount than the oxidized form of the mediator. While the above assays are described, it is contemplated that current, charge, impedance, conductance, potential, or other electrochemically indicated property of the sample might be accurately correlated to the concentration of the analyte in the sample with an electrochemical biosensor in accordance with this disclosure.

tures can be used as electrode traces in electrochemical sensors. The reagent can be applied to these structures using the above process.

Surprisingly, it has been found that the capillary channel and spacer structure of the sensor can be formed by using a double sided adhesive tape with a respective cutout as a spacer structure and covering parts of the reagent layer on the electrode substrate. Unexpectedly, no leakage of sample liquid can be observed at the positions where the double-sided adhesive tape covers the reagent film. Therefore, it is possible to first make structured electrode traces by a laser ablation process on a web material, then slot-die-coat the reagent material and subsequently define the active reagent area which comes into contact with the blood sample by using a respectively formed double sided adhesive spacer. This process can advantageously be used to eliminate tolerances in the production line. Especially, masking the reagent coating with the spacer can be used to precisely define the actual reaction area.

In the second aspect of the present invention, the invention concerns a method or process for producing a reagent layer on a solid support material using the shear thinning, slightly thixotropic or thixotropic reagent composition of the invention. The process includes providing a solid support material such as a web of plastics material like Melinex® 329 of DuPont. During the process of the present invention, the solid support material is moved relative to a slot-die-coating head. Usually, the solid support web material is transported in a reel-to-reel process across the slot of the die-coating head. However, it is also possible, to move the die-coating head and keep the web material stationary. During the movement of the web material relative to the die-coating head, a defined distance between the web and the die-coating head is maintained. Preferably, the coating gap is in the range of between 30 and 90 μm, typically between 68 and 83 μm, most preferred between 72 and 76 μm. By forcing the reagent composition through the slot of the slot-die-coating head, the reagent is deposited onto the solid support material, forming a continuous stripe of reagent on the solid support material. As mentioned above, the web material may comprise electrode traces and the reagent stripe may partly cover these traces. Preferably, in the dried state the reagent stripe has a width of less than 1 cm and a height of less than 10 μm.

Preferably, the solid support material is moved relative to the slot-die-coating head at a speed of between 20 and 80 m/min, most preferably at a speed of between 30 and 40 m/min.

Preferably, the reagent composition is delivered to the solid support material at a coating flux of 5.5 to 30 g/min, most preferably at a flux of 13 to 15 g/min.

Subsequently, the deposited reagent stripe is dried either under ambient conditions or in a heated airflow.

In a further aspect, the invention concerns analytical test elements that comprise the above reagent composition. Preferably, the analytical test elements of the present invention are manufactured according to the process as described above.

The invention has the following advantages:

1. Sensors requiring small sample volumes (typically 100 to 1000 nl) can easily be constructed using the slot die coated dry film and spacer/capillary channel lamination processes. The dry film stripe is of uniform thickness and is homogeneous over the electrochemical reaction area. The required capillary dimensions/imprecision of the sensor is dependent on the variation in spacer thickness and the construction of the capillary channel.

2. The slot-die-coating technology can be paired with a sophisticated layout of the electrodes design, thus enabling the capability of miniaturizing and creating multiple applications in the sensor capillary, (for example, staggering two or more lines/stripes of different reagents within an adequately designed layout of electrodes). Two staggered slot dies or a special slot die assembly designed for two or more fluids can be used to achieve this goal. The coating fluids preferably will have properly matching rheologic properties. The best technological case is achieved if the coating windows of the different fluids have a consistent overlapping region.

3. The slot-die-coating film application technology paired and combined with the rheological properties of the reagent enables homogeneous coatings using a reel to reel coating process for rapid production of diagnostic sensors.

4. Thixotropy or shear thinning behavior is the main rheologic feature of the fluid to be coated in respect to the mass distribution and its profile across the coated layer, impacting on the flatness, repeatability and homogeneity of the wet and dried layer. This feature is reached by using Xanthan gum, for example, Keltrol®, CMC and Silica in a concentration and combination to match the desired shear thinning, slightly thixotropic or thixotropic behavior of the coating fluid.

Surprisingly, it has been found that the role of silica, in particular the preferred untreated, hydrophilic silica, preferably with a particle size D50 (i.e., 50% of the particles have a size of the given size or below) of 1 to 7 μm, in the "wet" status (in the coating fluid) is that in combination with the film thickeners (Keltrol® and CMC, either one or both of them) silica increases the viscosity and enhances the shear thinning, slightly thixotropic or thixotropic behavior of the coating fluid.

Silica acts in the dried state to, among other things:

a) prevent back transfer of the dried film on the un-coated side of the foil/carrier if the web material is wound to rolls after the coating and drying processes, and b) enlarge the specific surface of the dried coating layer as compared to a smooth coating layer. Without wishing to be tied to any specific theory, this is likely due to the particle-size distribution of silica particles. Since the speed of fluid transport is increased by the ratio between the surface area and the fluid volume, this enlarged specific surface is speeding up the wetting process of the dried film and in consequence leads to a shorter capillary fill time.

The present invention is further elucidated by the following Examples and Figures. With respect to the Figures whenever possible like numbers, letters and symbols refer to like structures, features and elements. For example, unless otherwise stated in the application the following key applies:

1 indicates a web;
2 indicates a sputtered metal film;
3 indicates a working electrode of electrode pair 1;
3' indicates a working electrode of electrode pair 2;
4 indicates a reference/counter electrode of electrode pair 1;
4' indicates a reference/counter electrode of electrode pair 2;
5 indicates a reagent stripe 1;
5' indicates a reagent stripe 2;
6 indicates a spacer (e.g., double sided adhesive);
7 indicates a top foil; and
8 indicates a vent opening in top foil.

Figure 2:
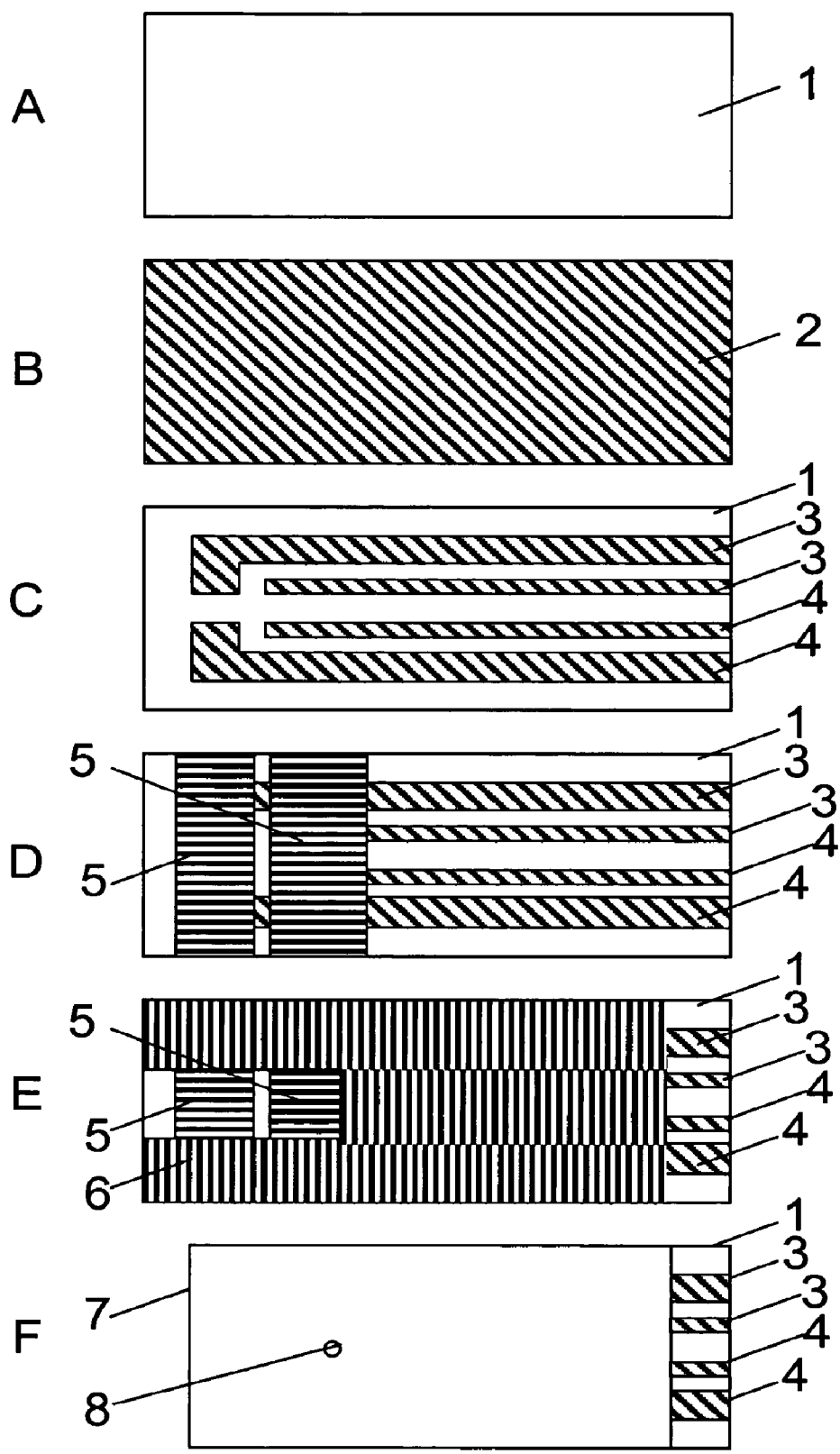
FIG. 2 shows schematically in 6 steps (A-F) how an electrochemical test element with two reagent zones is manufactured using the slot-die-coating process of the present invention.

FIGS. 1 and 2 are schematic representations of the several steps that are done during the manufacturing process for electrochemical test elements using the reagent composition and process of the present invention. A person of ordinary skill in the art would readily recognize that the process can be used with other electrode configurations and with multiple stripes having the same or different composition and different positions on the strip. It is to be noted that the processes described in FIGS. 1 and 2 could also be carried out without electrodes present on the test strips. A person of ordinary skill in the art would readily recognize that the process and reagent described herein can also be adapted to optical test elements as well.

Parts A and B of FIGS. 1 and 2 are identical and show a polymer web (1), preferably an inert plastic material such as Melinex® 329 of DuPont (see, e.g., part A), on which is coated a metal layer (2) (see, e.g., part B) by conventional techniques such as sputtering, chemical, electrochemical or physical vapor deposition, etc.

Preferably, the metal layer (2) subsequently is structured by for example a laser ablation process. This process removes parts of the metal layer (2) and discrete structures of metal which can act as electrodes (3, 4) remain on the surface of the polymer web (1). It should be understood, however, that conventional printing techniques or lithographic processes can also be used to create electrodes (3, 4) on the polymer web (1).

After the laser ablation step in FIG. 1, part C, two electrodes (3, 4) are formed on the polymer web. In FIG. 2, part C, two pairs of electrodes (3, 3', 4, 4') are formed.

In the next step (shown in part D of FIGS. 1 and 2), reagent stripes 5, 5' are deposited over the active area of the working and counter electrodes (3, 3', 4, 4'). The reagent composition is applied on the electrode structure by the slot-die-coating process of the present invention.

In part E of FIGS. 1 and 2, a spacer layer (6) is laminated to the electrode structure of part D of FIGS. 1 and 2. The spacer (6) is preferably a double-sided adhesive tape that covers all parts of the reagent and electrode structures that are not to be brought into contact with liquid sample. In addition, the spacer (6) has a cutout that defines the reactive area of the reagent and the underlying electrodes. At the opposite end of the spacer (6), i.e., the end where the electrode leads are located that are not covered by reagent composition, the spacer (6) leaves free parts of the electrode structures that can be used to connect the test strip to a respective test strip reading meter.

Spacer (6) preferably covers a narrow part (less than 2 mm) of the reagent (5 in FIG. 1, 5' in FIG. 2) to mask eventual inhomogeneous edge regions of the reagent coating.

After laminating the spacer (6) to the electrode and reagent web, in a preferred embodiment, part of the web material is cut off to trim the reagent stripe (5).

In part F of FIGS. 1 and 2, a top foil (7), preferably an inert plastics cover, is placed onto the surface of the spacer (6) that is not in contact with the polymer web (1). The polymer web (1), the spacer (6) and the top foil (7) form a 3D capillary channel which is defined by the thickness of the spacer (6) and the dimensions of the cut-out in the spacer. To enable a filling of the capillary space, preferably either the top foil (7) or the polymer web (1) has a vent opening (8).

As is clear for those skilled in the art, the surfaces of either the polymer web (1) or the top foil (7) that face the capillary space can be rendered hydrophilic by a respective hydrophilic treatment, for example, by coating with a surfactant or plasma treatment.

EXAMPLES

The following Examples provided by way of illustration and not by way of limitation, will disclose more details of the invention:

Example 1

Reagent Composition for Use in an Electrochemical Amperometric Glucose Biosensor An aqueous mixture of the following components was prepared:

| Substance | Source | % w/w |
|---|---|---|
| Keltrol ® F (Xanthan gum) | Kelco | 0.2136% |
| Carboxymethyl cellulose (CMC) | Hercules-Aqualon | 0.5613% |
| Polyvinylpyrrolidone (PVP) K25 | BASF | 1.8952% |

-continued

| Substance | Source | % w/w |
|---|---|---|
| Propiofan ® (polyvinylchloride) (50% water) | BASF | 2.8566% |
| Glucose-dye-oxidoreductase (GlucDOR) (E.C. 1.1.99.17) | Roche Diagnostics | 0.3310% |
| pyrroloquinoline quinine (PQQ) | Roche Diagnostics | 0.0092% |
| Sipernat ® 320 DS (synthetic, amorphous precipitated silica) | Degussa Hüls | 2.0039% |
| Na-Succinat × 6 $H_2O$ | Mallinckrodt Chmeicals | 0.4803% |
| Trehalose | Sigma-Aldrich | 0.4808% |
| $KH_2PO_4$ | J. T. Baker | 0.4814% |
| $K_2HPO_4$ | J. T. Baker | 1.1166% |
| N,N-Bis-(hydroxyethyl)-3-methoxy-p-nitroso aniline | Roche Diagnostics | 0.6924% |
| Mega 8 ® (n-Octanoyl-N-methylglucamide) | Dojindo | 0.2806% |
| Geropon ® T 77 (Sodium N-methyl N-oleyl taurate) | Rhodia Chimie | 0.0298% |
| KOH | Merck | 0.1428% |
| Water, double distilled | | 89.9558% |

The reagent matrix was custom modified to meet the demands of the slot-die-coating process. Silica, Keltrol® (Xanthan Gum), carboxymethyl cellulose (CMC) and surfactants were added to the coating matrix to modify the rheology of the reagent mass. Surfactant concentrations were adjusted to obtain surface tensions (measured with a Tensiometer K10T (Kruess)) in the most preferred range of 33 to 42 mN/m. Surface tension in this range promotes better adhesion and controlled spreading of the coated stripe on the web. The most preferred viscosity range measured using a Rheomat 115 (Contraves) for the coating mass is 95 to 115 mPa-s. The polymers and the silica also impart thixotropic behavior to the coating. Coatings shear thin as they are dispensed through the slot die head onto the web. This reduces the apparent viscosity of the coating.

Figure 3:
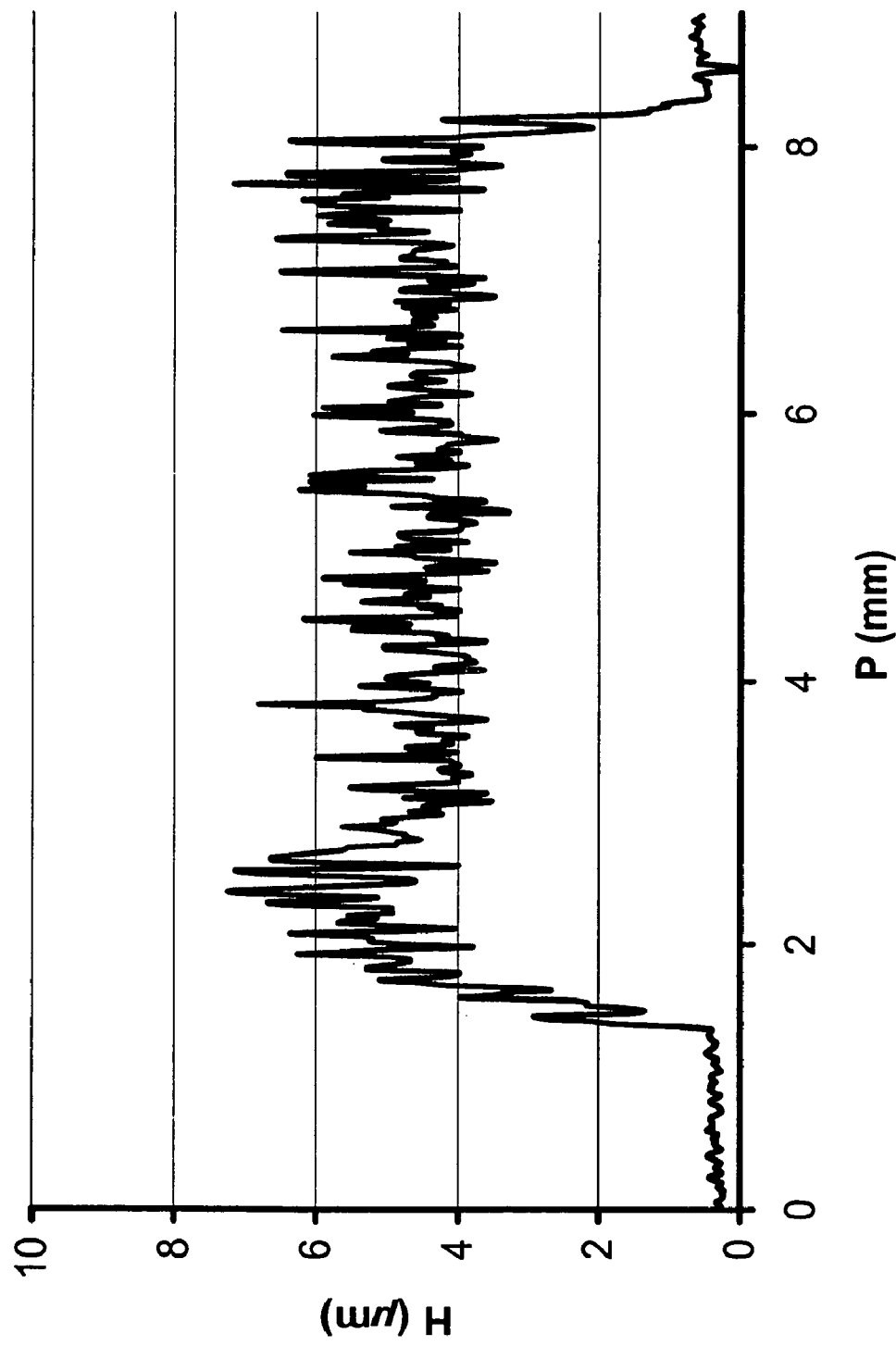
FIG. 3 shows the results of a profilometric measurement across the reagent stripe according to Example 1.
Figure 4A:
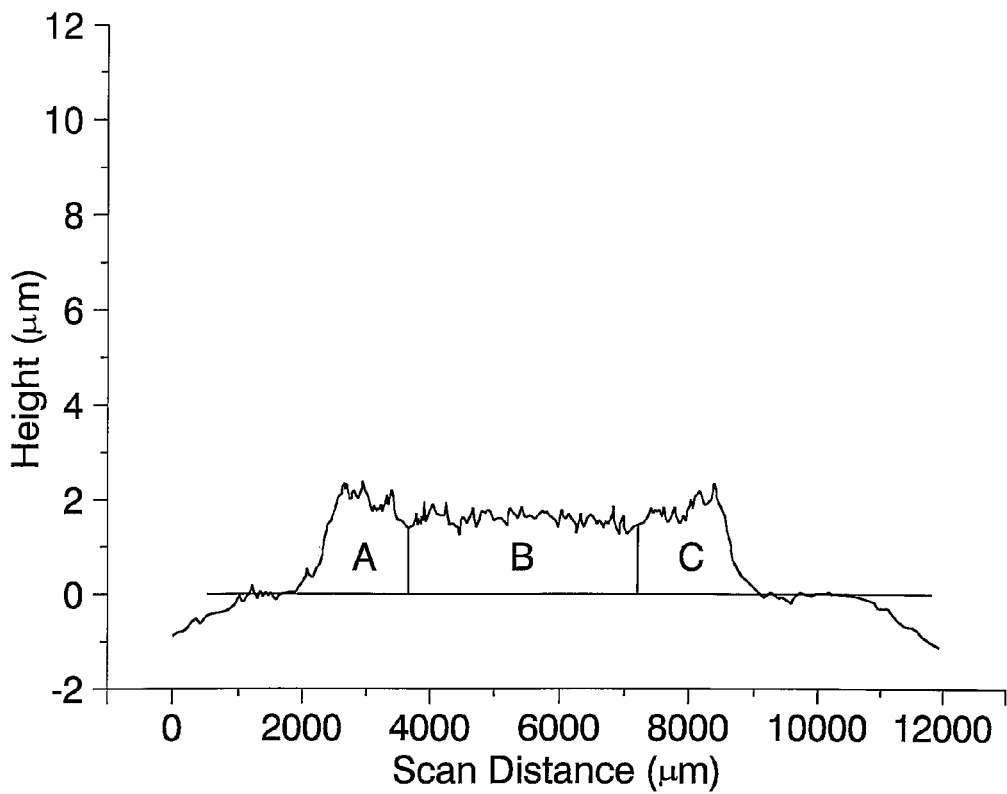
FIG. 4 represents the data of profilometric measurements across reagent stripes according to the present invention.
Figure 4B:
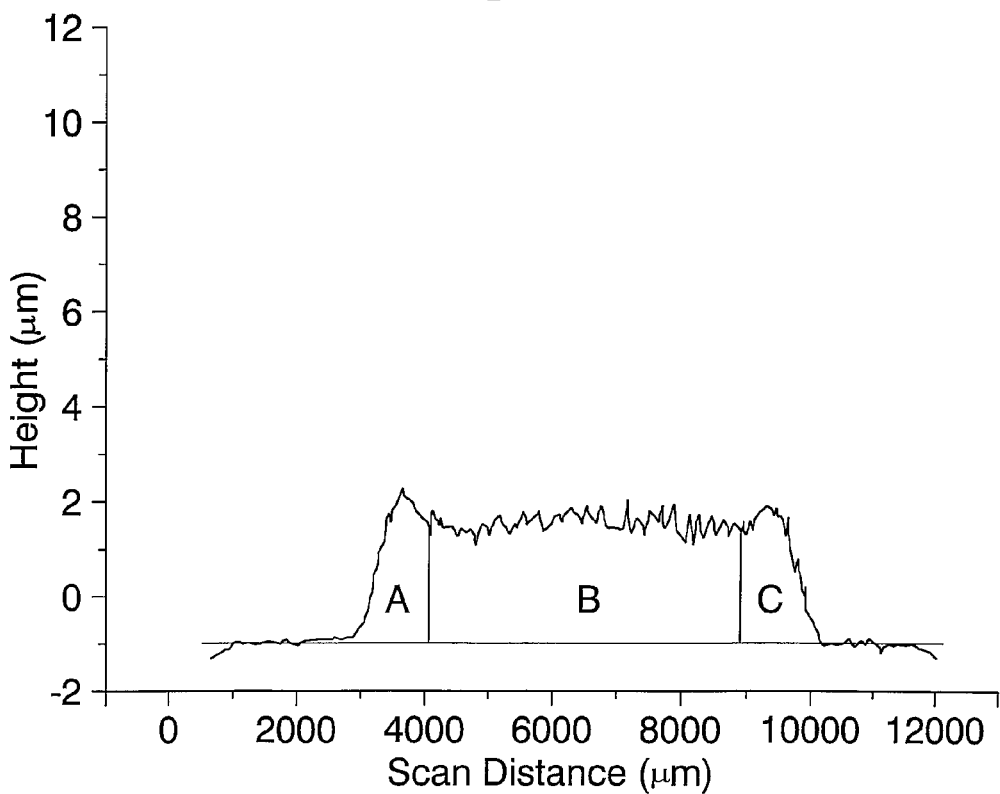
Figure 4C:
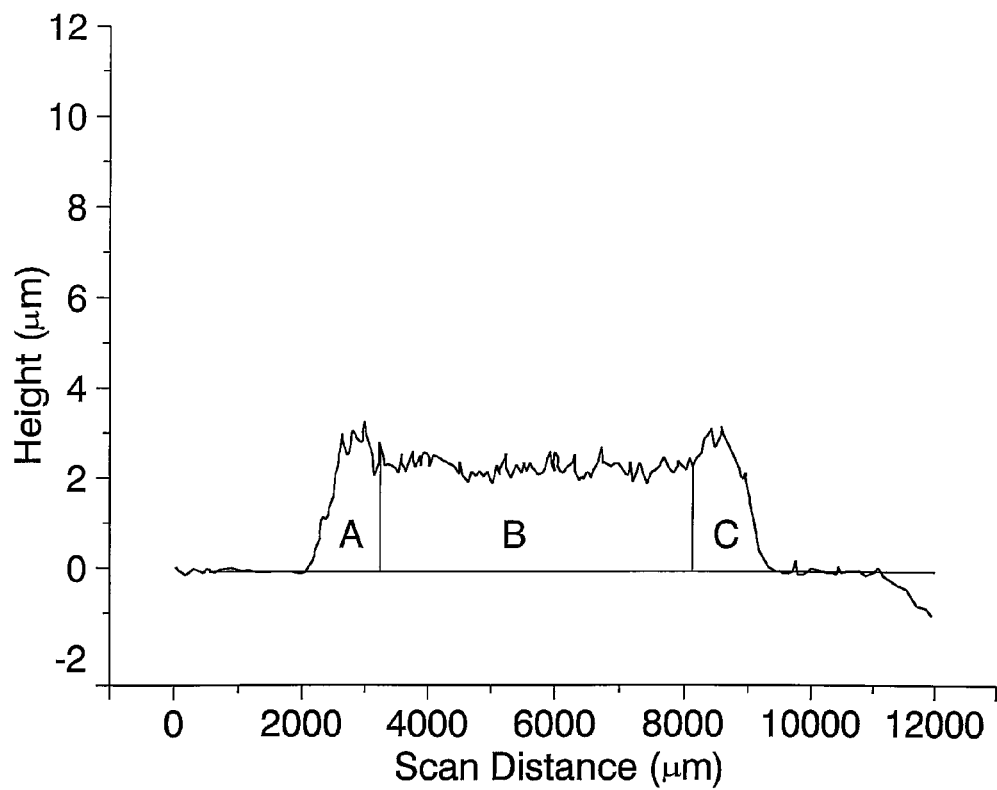
Figure 4D:
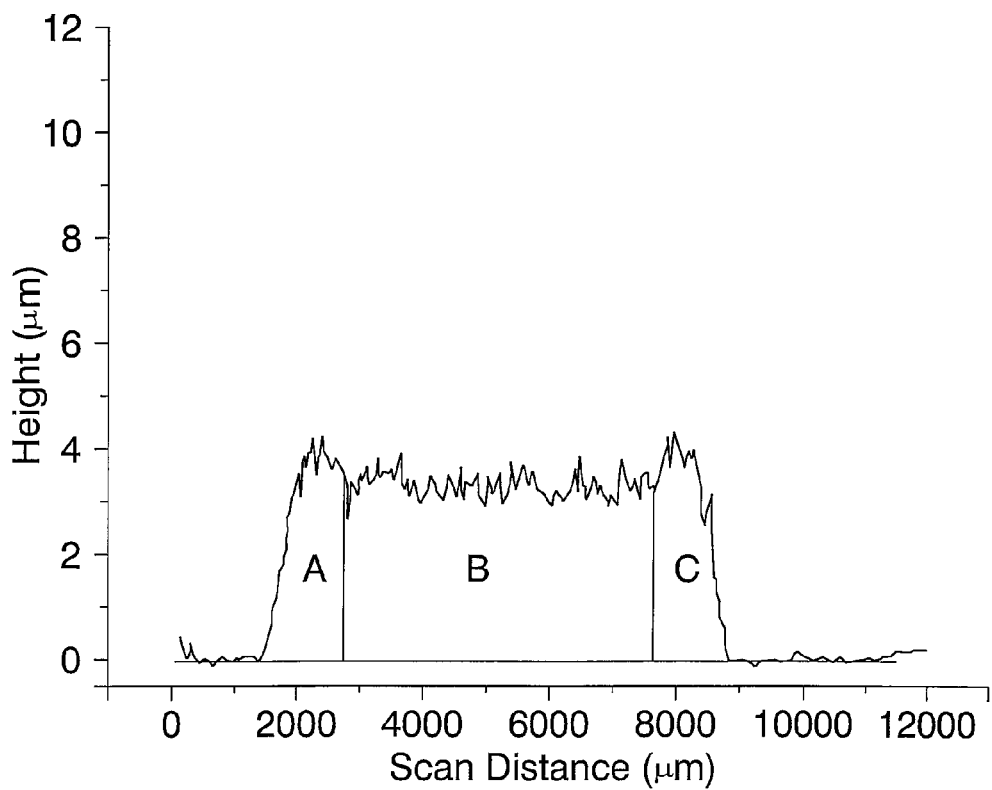
Figure 4E:
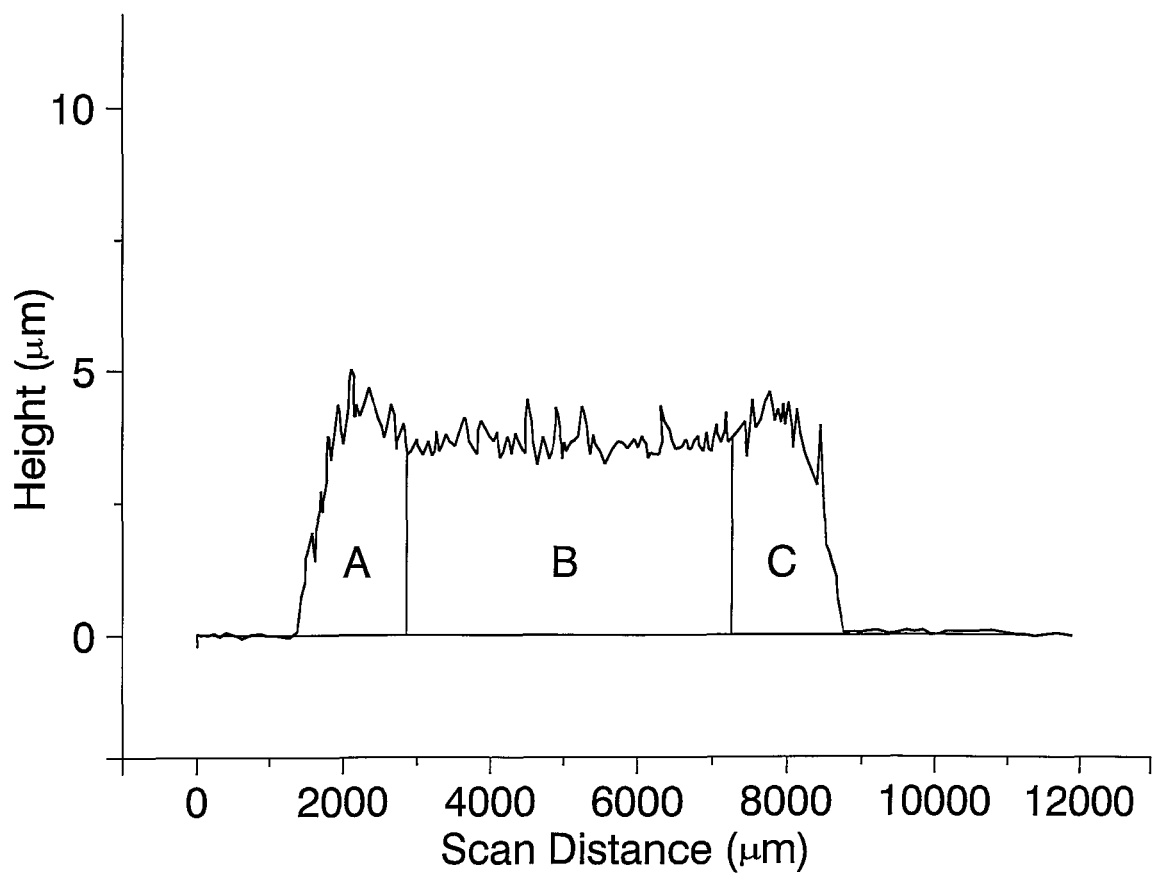

Stripes of reagent coating mass with these lower viscosities show a migration of the stripe edges and reagent components toward the center of the stripe during the drying process. This migration leads to an irregular and irreproducible surface profile in the middle of the dried stripe. Dispense of coatings having shear thinning, slightly thixotropic or thixotropic properties show the same shear thinning effects. However, the viscosity of the coated stripe returns to near the apparent viscosity shortly after being dispensed and before entering the drying region. The migration of the stripe edges towards the center during drying is retarded. As illustrated in FIG. 3, this leads to a flat reproducible region in the center of the stripe, in the reaction area. Thinner films further retard the migration of the coating edges to the center of the coated stripe.

Example 2

Reagent Composition for an Electrochemical Amperometric Coagulation Sensor

An aqueous mixture of the following components was prepared:

| Substance | Source | End Concentration in Reagent |
|---|---|---|
| Glycine | Sigma | 23 g/l |
| Polyethylenglycol | Sigma | 23 g/l |
| Sucrose | Sigma | 55 g/l |
| Bovine Serum Albumin | Sigma | 6.9 g/l |
| Mega 8 ® (n-Octanoyl-N-methylglucamide) | Dojindo | 1 g/l |
| Resazurin | Sigma-Aldrich Chemie GmbH | 1.4 g/l 5.6 mmol/l |
| Polybrene ® (hexadimethrine bromide) | Sigma | 0.015 g/l |
| Moviol ® 4/86 (poly vinyl alcohol) | Clariant GmbH | 20 g/l |
| Keltrol ® F (Xanthan gum) | Kelco | 2.89 g/l |
| Electrozym TH (reduced Chromozym TH; reduced tosyl-glycyl-prolyl-arginine-4-nitranilide acetate) | Roche Diagnostics | 1.226 g/l 1.9 mmol/l |
| soy bean phospholipids | | |
| solution of recombinant tissue factor | Dade-Behring | 109 µg/l |

Example 3

Alternative Reagent Composition for an Electrochemical Amperometric Glucose Biosensor An aqueous mixture of the following components was prepared:

| Substance | Source | % w/w |
|---|---|---|
| Keltrol ® F (Xanthan gum) | Kelco | 0.20% |
| Gantrez ® S97 (Methyl vinylether/maleic anhydride copolymer) | ISP | 2.48 |
| Polyvinylpyrrolidone (PVP) K25 | BASF | 1.93% |
| Propiofan ® (polyvinylchloride) (50% water) | BASF | 2.94% |
| Glucose-dye-oxidoreductase (GlucDOR) (E.C. 1.1.99.17?) | Roche Diagnostics | 0.33% |
| pyrroloquinoline quinine (PQQ) | Roche Diagnostics | 0.0093% |
| Silica FK 300 DS | Degussa Hüls | 1.77% |
| $KH_2PO_4$ | J. T. Baker | 0.48% |
| $K_2HPO_4$ | J. T. Baker | 1.47% |
| N,N-Bis-(hydroxyethyl)-3-methoxy-p-nitroso aniline | Roche Diagnostics | 0.69% |
| Mega 8 ® (n-Octanoyl-N-methylglucamide) | Dojindo | 0.29% |
| Geropon ® T 77 (Sodium N-methyl N-oleyl taurate) | Rhodia Chimie | 0.030% |
| KOH | Merck | 1.14% |
| Water, double distilled | | 86.227% |

Example 4

Alternative Reagent Composition for an Electrochemical Amperometric Glucose Biosensor An aqueous mixture of the following components was prepared:

| Substance | Source | % w/w |
|---|---|---|
| Keltrol ® F (Xanthan gum) | Kelco | 0.20% |
| Gantrez ® S97 (Methyl vinylether/maleic anhydride copolymer) | ISP | 0.50% |
| Carboxymethyl cellulose (CMC) | Hercules-Aqualon | 0.50% |
| Polyvinylpyrrolidone (PVP) K25 | BASF | 1.90% |
| Propiofan ® (polyvinylchloride) (50% water) | BASF | 2.89% |
| Glucose-dye-oxidoreductase (GlucDOR) (E.C. 1.1.99.17?) | Roche Diagnostics | 0.34% |
| pyrroloquinoline quinine (PQQ) | Roche Diagnostics | 0.0093% |
| $KH_2PO_4$ | J. T. Baker | 0.48% |
| $K_2HPO_4$ | J. T. Baker | 1.46% |
| N,N-Bis-(hydroxyethyl)-3-methoxy-p-nitroso aniline | Roche Diagnostics | 0.71% |
| Mega 8 ® (n-Octanoyl-N-methylglucamide) | Dojindo | 0.28% |
| Geropon ® T 77 (Sodium N-methyl N-oleyl taurate) | Rhodia Chimie | 0.030% |
| KOH | Merck | 0.31% |
| Water, double distilled | | 90.384% |

Example 5

Coating Process

The polymer web (Melinex® 329, DuPont) is moved into the coating area, containing a slot die head and a back up roller. The slot die head (TSE, Switzerland) is zeroed to the web surface and adjusted to a slot to web gap of 74 µm. Web speed is ramped up from 0 to 38 m/min for deposition of coating on the web. The reagent matrix can be delivered to the slot die head using a variety of means including gear pumps, pistons, syringes, bladder systems. The reagent delivery system is adjusted to a water flow of 13.58 ml/min to deliver a coat weight of 53 g/m² through the coating head. The width of the resulting coated stripe is 7.0±0.3 mm. The coating is dried in the heated drying zone (length 15 m, temperature 110° C., at a speed of 38 m/min) and rewound on spools at the rewind station.

FIGS. 3 to 5 show the results of profilometric measurements across the reagent stripe according to this example. The profilometer system used was a Dektak IIA Surface Profile Measuring System (Veeco Instruments Inc., Sloan Technology Division, Dallas, Tex.). Profile data from the Dektak IIA were baseline corrected.

In FIG. 3, P (mm) denotes the x-position of the scan across the web and reagent stripe (in mm) and H (µm) denotes the respective relative height of the coating (in µm). The reagent mass was prepared according to Example 1. As can be seen, the reagent stripe has a cross-sectional width of about 7 mm and a respective average center height of approximately 5 µm. The edges of the reagent coating are relatively sharp. The homogeneous plateau region of the coating fills approximately 80% of the reagent stripe width.

The profile of the reagent coating as depicted in FIG. 3 is typical for coatings according to the present invention. For reagent stripes of 10 mm or less in width, sharp edges can be obtained, which ramp up from the underlying web material (corresponding to a coating height of zero) to the plateau region in the center of the coating within 1 mm on each side or less (i.e. 80% or more of the coating belong to the homogeneous center plateau region). Within the center region, the reagent coating is practically uniform in thickness.

FIG. 4 shows the results of profilometric measurements across the reagent stripe prepared according to this example. Scan Distance (μm) denotes the x-position of the scan across the web and reagent stripe (in μm) and Height (μm) denotes the respective relative height of the coating (in μm). The reagent mass was prepared according to Example 1 with milled silica. FIGS. 4A to 4E give the results for coating weights of 20, 25, 30, 40 and 50 mg/m², respectively.

FIG. 5 illustrates the results of profilometric measurements across a reagent stripe prepared according to a comparative example, i.e., not in accordance with the teachings of the present invention. Scan Distance (μm) denotes the x-position of the scan across the web and reagent stripe (in μm) and Height (μm) denotes the respective relative height of the coating (in μm). The reagent mass was prepared according to Example 1 however without the presence of the rheological modifiers Keltrol®, CMC and silica.

Figure 5B:
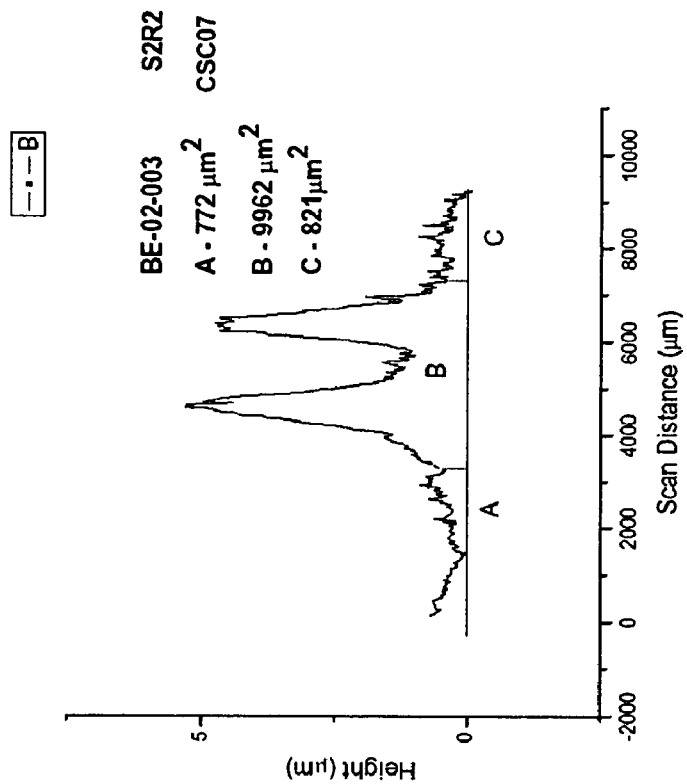
FIG. 5 represents the data of profilometric measurements across reagent stripes without the use of rheological modifiers of the present invention.
Figure 5A:
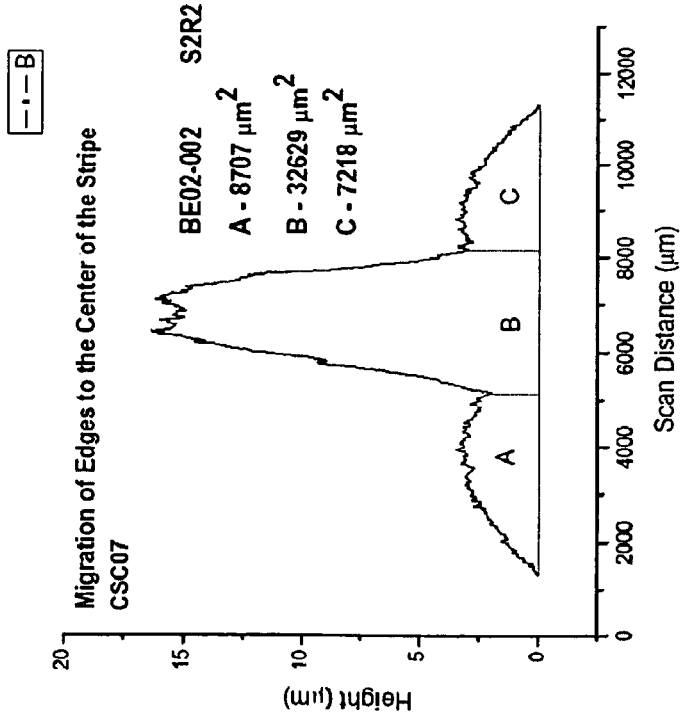

FIGS. 5A and 5B show that without rheological modifiers the dried reagent coating tends to form inhomogeneous reagent stripes on the web material. In FIG. 5A, the reagent concentrates in the center portion of the coated stripe; in FIG. 5B, the reagent concentrates in two regions located between the center and the edge portions of the reagent stripes. In both cases, the edge portions are depleted from reagent.

Comparison of FIG. 5 (comparative example) with FIGS. 3 and 4 (both according to the present invention) reveals the advantageous effects of the reagent composition and process of the present invention.

Figure 6:
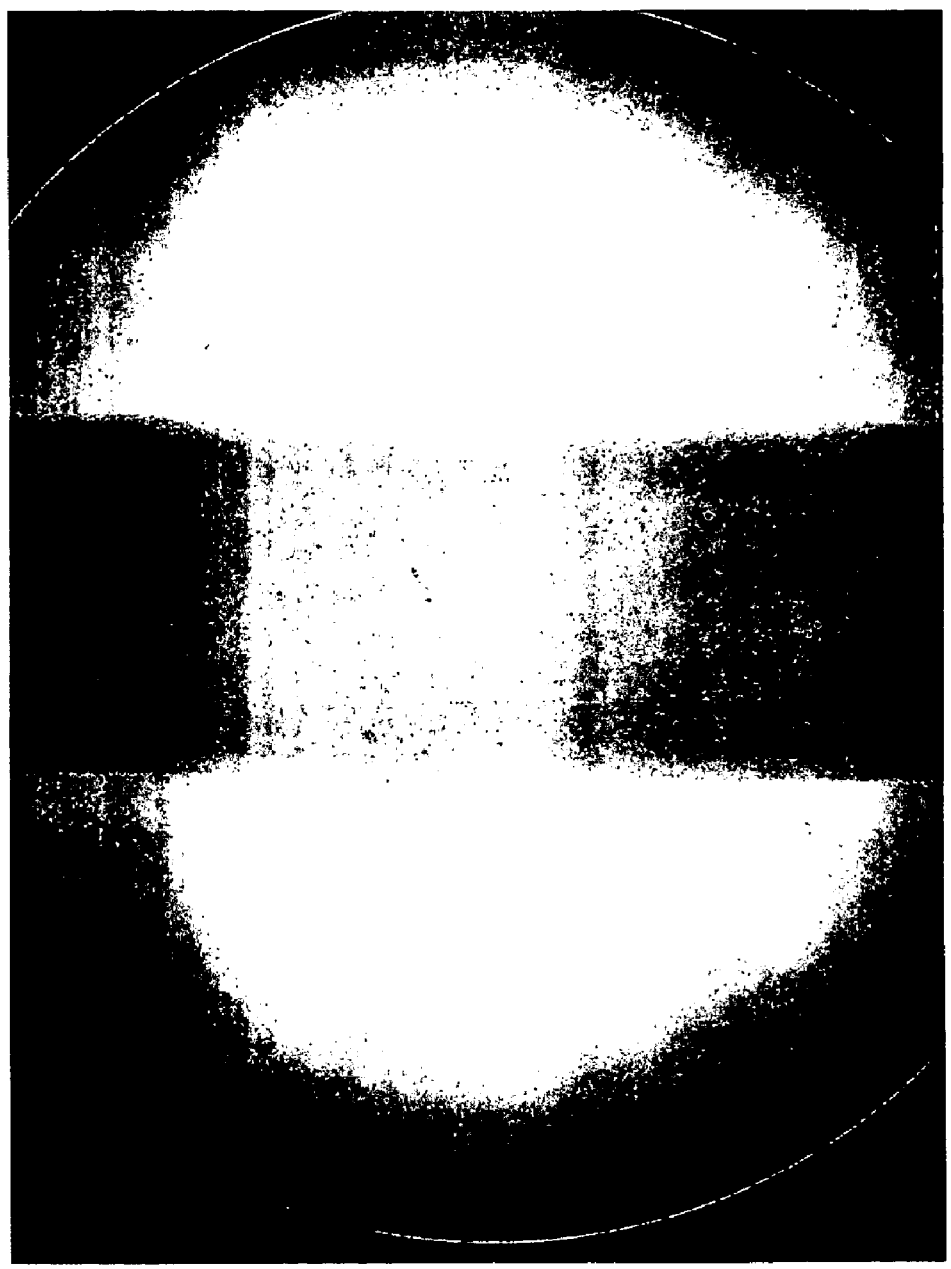
FIG. 6 is a photograph of a microscope view of a reagent stripe coated onto a web material according to the present invention.

FIG. 6 is a photograph of a microscope view of a reagent stripe (central dark rectangular area) coated onto a web material (light areas around the central stripe) from a reagent composition according to Example 1 (and comparable to the profilometric data shown in FIG. 4). Coating was done according to Example 5. The coated stripe shows good homogeneity across the coating direction (coating direction was from top to bottom) as well as along this direction.

Figure 7:
FIG. 7 shows two photographs (FIGS. 7A and 7B) of a microscope view of a reagent stripe coated onto a web material without the use of rheological modifiers of the present invention.
Figure 7:

In stark contrast to the smooth and uniform reagent layer shown in FIG. 6, FIGS. 7A and 7B are photographs of microscope views (comparative examples) of reagent stripes coated onto web material with profilometric data comparable to that shown in FIG. 5. Coating was done according to Example 5; however, the reagent did not contain the rheological modifiers. The coated stripes clearly show inhomogeneities across the coating direction (coating direction was from top to bottom). For example, regions of thicker reagent are manifested by the dark bands running along the stripes. FIG. 7A shows one such dark band positioned in about the middle of the stripe (compare FIG. 5A), whereas FIG. 7B shows two dark bands (compare FIG. 5B). These one or two regions of thicker reagent coatings (dark zones) within the reagent stripe are believed due to drying effects of the reagent coating materials.

Example 6

Variation of Rheological Modifiers in the Reagent Composition of Example 1

In the reagent composition of Example 1 the contents of the ingredients CMC, Keltrol®, Propiofan® and PVP were varied in accordance with the following Table. Ingredient contents are given in % w/w and viscosity is given in mPa-s.

| CMC | Keltrol® | PVP | Propiofan® | Silica | Viscosity | Thixotrophic |
|---|---|---|---|---|---|---|
| 0.56 | 0.21 | 1.9 | 2.86 | 2 | 117 | yes |
| 0.476 | 0.28 | 1.52 | 2.29 | 2 | 99 | yes |
| 0 | 0.77 | 1.52 | 2.29 | 2 | 69.5 | yes |
| 0.77 | 0 | 2.28 | 3.43 | 2 | 149 | yes |
| 0.504 | 0.4 | 1.9 | 2.86 | 2 | 123 | weak |

All publications, patents and patent applications cited in this specification are herein incorporated by reference, as if each individual publication, patent, or patent application was specifically and individually indicated to be incorporated by reference and set forth in its entirety herein.

While preferred embodiments incorporating the principles of the present invention have been disclosed hereinabove, the present invention is not limited to the disclosed embodiments. Instead, this application is intended to cover such departures from the present disclosure as come within known or customary practice in the art to which this invention pertains and which fall within the limits of the appended claims.

What is claimed is:

1. A process for producing a reagent layer on a solid support material, comprising the steps of:
   providing a solid support material;
      moving said solid support material relative to a slot-die-coating head;
   maintaining a defined distance between the surface of said solid support material and said slot-die-coating head;
   depositing a shear thinning, at least slightly thixotropic reagent through said slot-die-coating head to create a continuous stripe of reagent on said solid support material, wherein said reagent has a viscosity of between about 95 to 115 mPa-s and a surface tension of between about 33 and 42 mN/m; and
   drying the coated reagent stripe on said support material.

2. The process according to claim 1, wherein said reagent is deposited on said solid support at a coating flux rate of about 5.5 to about 30 g/min.

3. The process according to claim 1, wherein said reagent is deposited on said solid support at a coating flux rate of about 13 to about 15 g/min.

4. The process according to claim 1, wherein said defined distance between said slot-die-coating head and said support material is between 30 and 90 μm.

5. The process according to claim 1, wherein said support material moves relative to said slot-die-coating head at a rate of between 20 and 80 m/min.

6. The process according to claim 1, wherein said support material moves relative to said slot-die-coating head at a rate of between 30 and 40 m/min.

7. The process according to claim 1, wherein said stripe of reagent is less than 1 cm wide.

8. The process according to claim 1, wherein after drying, said reagent on said solid support material has a height of less than 10 μm.

9. The process according to claim 1, said reagent including at least one of buffers, enzymes, mediators, stabilizers, thickeners, proteins, indicators, dyes, film formers, surfactants and co-factors.

10. The process according to claim 9, said reagent further including at least one of silica, xanthan gum and CMC.

11. The process according to claim 9, said reagent further including silica and at least one of xanthan gum and CMC.

12. The process according to claim 9, said reagent further including silica, xanthan gum and CMC.

13. In a process for preparing biosensors from a webbing of a substrate, the improvement comprising:
depositing a continuous stripe of reagent onto the webbing in the form of a shear thinning, at least slightly thixotropic reagent having a viscosity of between about 95 to 115 mPa-s and a surface tension of between about 33 and 42 mN/m; and
drying the coated reagent stripe on said support material.

14. A process for preparing biosensors comprising:
depositing a continuous stripe of reagent onto a webbing in the form of a shear thinning, at least slightly thixotropic reagent having a viscosity of between about 95 to 115 mPa-s and a surface tension of between about 33 and 42 mN/m;
applying a spacer layer over the reagent; and
attaching the spacer layer to the webbing.

* * * * *